(12) United States Patent
Leonard et al.

(10) Patent No.: US 12,053,588 B2
(45) Date of Patent: *Aug. 6, 2024

(54) SYSTEMS AND METHODS FOR HUMIDITY CONTROL

(71) Applicant: Vapotherm, Inc., Exeter, NH (US)

(72) Inventors: Scott A. Leonard, Exeter, NH (US); Meghan H. Kate, Deerfield, NH (US)

(73) Assignee: VAPOTHERM, INC., Exeter, NH (US)

( * ) Notice: Subject to any disclaimer, the term of this patent is extended or adjusted under 35 U.S.C. 154(b) by 748 days.

This patent is subject to a terminal disclaimer.

(21) Appl. No.: 16/785,303

(22) Filed: Feb. 7, 2020

(65) Prior Publication Data

US 2020/0246577 A1   Aug. 6, 2020

Related U.S. Application Data

(62) Division of application No. 14/587,898, filed on Dec. 31, 2014, now Pat. No. 10,596,345.

(51) Int. Cl.
*A61M 16/16* (2006.01)
*A61M 16/00* (2006.01)
(Continued)

(52) U.S. Cl.
CPC ...... *A61M 16/161* (2014.02); *A61M 16/0003* (2014.02); *A61M 16/0875* (2013.01);
(Continued)

(58) Field of Classification Search
CPC .. A61M 16/14; A61M 16/142; A61M 16/145; A61M 16/161; A61M 16/16;
(Continued)

(56) References Cited

U.S. PATENT DOCUMENTS 2,414,747 A    1/1947  Kirschbaum
2,742,040 A    4/1956  Moore et al.
(Continued)

FOREIGN PATENT DOCUMENTS

AU    2013313726 B2    5/2016
AU    2016219577 B2    4/2018
(Continued)

OTHER PUBLICATIONS

International Search Report and Written Opinion for International Application No. PCT/US2007/021469 dated Oct. 13, 2008.
(Continued)

*Primary Examiner* — Colin W Stuart
*Assistant Examiner* — Douglas Y Sul
(74) *Attorney, Agent, or Firm* — McDermott Will & Emery LLP

(57) ABSTRACT

Systems, methods, and devices for humidifying a breathing gas using a vapor transfer unit are presented. The method includes providing a first vapor transfer unit having a gas passage and a liquid passage, delivering a liquid to the liquid passage, delivering a gas to the gas passage, humidifying the gas by delivering vapor from the liquid in the liquid passage to the gas in the gas passage, exiting the humidified gas outside the vapor transfer unit at first relative humidity and at a high gas flow rate, and reducing the gas flow rate through the first vapor transfer unit to less than a low gas flow rate, while preventing the relative humidity from exceeding the first relative humidity by more than an acceptable margin.

22 Claims, 15 Drawing Sheets

(51) Int. Cl.
*A61M 16/08* (2006.01)
*A61M 16/10* (2006.01)
*A61M 16/14* (2006.01)
*A61M 16/20* (2006.01)

(52) U.S. Cl.
CPC .......... *A61M 16/145* (2014.02); *A61M 16/16* (2013.01); *A61M 16/20* (2013.01); *A61M 16/107* (2014.02); *A61M 16/109* (2014.02); *A61M 2205/3327* (2013.01)

(58) Field of Classification Search
CPC ............... A61M 16/20; A61M 16/0875; Y10T 137/87539; Y10T 137/87547
See application file for complete search history.

(56) References Cited

U.S. PATENT DOCUMENTS

| | | |
|---|---|---|
| 3,659,604 A | 5/1972 | Melville et al. |
| 3,734,091 A | 5/1973 | Taplin |
| 3,871,373 A | 3/1975 | Jackson |
| 3,903,216 A | 9/1975 | Allan et al. |
| 3,923,057 A | 12/1975 | Chalon |
| 4,010,748 A | 3/1977 | Dobritz |
| 4,013,742 A | 3/1977 | Lang |
| 4,028,444 A | 6/1977 | Brown et al. |
| 4,028,445 A | 6/1977 | Hickmann et al. |
| 4,036,919 A | 7/1977 | Komendowski et al. |
| 4,051,205 A | 9/1977 | Grant |
| 4,098,853 A | 7/1978 | Brown et al. |
| 4,110,419 A | 8/1978 | Miller |
| 4,152,379 A | 5/1979 | Suhr |
| 4,163,371 A | 8/1979 | Groninger |
| 4,172,105 A | 10/1979 | Miller et al. |
| 4,288,396 A | 9/1981 | Ottestad |
| 4,319,566 A | 3/1982 | Hayward et al. |
| 4,325,413 A | 4/1982 | Lenhart et al. |
| 4,354,984 A | 10/1982 | Richardson et al. |
| 4,366,105 A | 12/1982 | Nowacki |
| 4,369,777 A | 1/1983 | Lwoff et al. |
| 4,381,267 A | 4/1983 | Jackson |
| 4,430,994 A | 2/1984 | Clawson et al. |
| 4,463,755 A | 8/1984 | Suzuki |
| 4,500,480 A | 2/1985 | Cambio, Jr. |
| 4,531,551 A | 7/1985 | Eichelberger et al. |
| 4,532,088 A | 7/1985 | Miller |
| 4,584,996 A | 4/1986 | Blum |
| 4,589,409 A | 5/1986 | Chatburn et al. |
| 4,621,633 A | 11/1986 | Bowles et al. |
| 4,632,677 A | 12/1986 | Blackmer |
| 4,644,790 A | 2/1987 | Mizoguchi |
| 4,648,395 A | 3/1987 | Sato et al. |
| 4,652,408 A | 3/1987 | Montgomery |
| 4,657,713 A | 4/1987 | Miller |
| 4,665,911 A | 5/1987 | Williams et al. |
| 4,682,010 A | 7/1987 | Drapeau et al. |
| 4,753,758 A | 6/1988 | Miller |
| 4,765,327 A | 8/1988 | Shim |
| 4,765,340 A | 8/1988 | Sakai et al. |
| 4,801,385 A | 1/1989 | Sachtler et al. |
| 4,810,854 A | 3/1989 | Jursich et al. |
| 4,838,258 A | 6/1989 | Dryden et al. |
| 4,859,331 A | 8/1989 | Sachtler et al. |
| 4,889,116 A | 12/1989 | Taube |
| 4,910,384 A | 3/1990 | Silver |
| 4,921,642 A | 5/1990 | LaTorraca |
| 4,941,469 A | 7/1990 | Adahan |
| 4,943,704 A | 7/1990 | Rabenau et al. |
| 4,955,372 A | 9/1990 | Blackmer et al. |
| 4,957,107 A | 9/1990 | Sipin |
| 4,973,231 A | 11/1990 | Colliver |
| 5,003,985 A | 4/1991 | White et al. |
| 5,005,569 A | 4/1991 | Pasternack |
| 5,031,612 A | 7/1991 | Clementi |
| 5,036,847 A | 8/1991 | Boussignac et al. |
| 5,038,840 A | 8/1991 | Fair |
| 5,065,756 A | 11/1991 | Rapoport |
| 5,103,814 A | 4/1992 | Maher |
| 5,178,151 A | 1/1993 | Sackner |
| 5,255,674 A | 10/1993 | Oftedal et al. |
| 5,329,939 A | 7/1994 | Howe |
| 5,336,156 A | 8/1994 | Miller et al. |
| 5,349,946 A * | 9/1994 | McComb ............ A61M 16/147 128/203.12 |
| 5,367,604 A | 11/1994 | Murray |
| 5,388,575 A | 2/1995 | Taube |
| 5,392,770 A | 2/1995 | Clawson et al. |
| 5,431,885 A | 7/1995 | Zlotnik et al. |
| 5,445,143 A | 8/1995 | Sims |
| 5,454,368 A | 10/1995 | Tarulli |
| 5,474,062 A | 12/1995 | DeVires et al. |
| 5,529,060 A | 6/1996 | Salmon et al. |
| 5,558,084 A | 9/1996 | Daniell et al. |
| 5,572,992 A | 11/1996 | Kankkunen et al. |
| 5,577,494 A | 11/1996 | Kuypers et al. |
| 5,588,423 A | 12/1996 | Smith |
| 5,623,922 A | 4/1997 | Smith |
| 5,640,951 A | 6/1997 | Huddart et al. |
| 5,724,957 A | 3/1998 | Rubsamen et al. |
| 5,769,071 A | 6/1998 | Turnbull |
| 5,823,184 A | 10/1998 | Gross |
| 5,901,705 A | 5/1999 | Leagre |
| 6,010,118 A | 1/2000 | Milewicz |
| 6,041,777 A | 3/2000 | Faithfull et al. |
| 6,050,260 A | 4/2000 | Daniell et al. |
| 6,078,730 A | 6/2000 | Huddart et al. |
| 6,095,505 A | 8/2000 | Miller |
| 6,102,037 A | 8/2000 | Koch |
| 6,125,847 A | 10/2000 | Lin |
| 6,129,082 A | 10/2000 | Leagre |
| 6,142,971 A | 11/2000 | Daoud et al. |
| 6,152,132 A | 11/2000 | Psaros |
| 6,167,883 B1 | 1/2001 | Beran et al. |
| 6,186,142 B1 | 2/2001 | Schmidt et al. |
| 6,216,691 B1 | 4/2001 | Kenyon et al. |
| 6,244,576 B1 | 6/2001 | Tsai |
| 6,256,454 B1 | 7/2001 | Dykes |
| 6,349,724 B1 | 2/2002 | Burton et al. |
| 6,397,841 B1 | 6/2002 | Kenyon et al. |
| 6,398,197 B1 | 6/2002 | Dickinson et al. |
| 6,410,465 B1 | 6/2002 | Lim et al. |
| 6,454,997 B1 | 9/2002 | Divino, Jr. et al. |
| 6,510,848 B1 | 1/2003 | Gibertoni |
| 6,536,428 B1 | 3/2003 | Smith et al. |
| 6,550,476 B1 | 4/2003 | Ryder |
| 6,554,260 B1 | 4/2003 | Lipscombe et al. |
| 6,560,408 B2 | 5/2003 | Glucksman et al. |
| 6,561,187 B2 | 5/2003 | Schmidt et al. |
| 6,613,280 B2 | 9/2003 | Myrick et al. |
| 6,718,974 B1 | 4/2004 | Moberg |
| 6,769,430 B1 | 8/2004 | Carlsen et al. |
| 6,824,127 B2 | 11/2004 | Park et al. |
| 6,827,046 B2 | 12/2004 | Welle |
| 6,827,084 B2 | 12/2004 | Grubb, Jr. |
| 6,904,911 B2 | 6/2005 | Gibertoni |
| 6,912,977 B2 | 7/2005 | Cumming |
| 6,918,389 B2 | 7/2005 | Seakins et al. |
| 6,935,337 B2 | 8/2005 | Virr et al. |
| 6,938,619 B1 | 9/2005 | Hickle |
| 6,938,886 B2 | 9/2005 | Glucksman |
| 6,953,354 B2 | 10/2005 | Edirisuriya et al. |
| 6,988,497 B2 | 1/2006 | Levine |
| 6,997,183 B2 | 2/2006 | Koch et al. |
| 7,051,733 B2 | 5/2006 | Gradon et al. |
| 7,066,452 B2 | 6/2006 | Rotering et al. |
| 7,073,500 B2 | 7/2006 | Kates |
| 7,077,135 B2 | 7/2006 | Pagan |
| 7,080,645 B2 | 7/2006 | Genger et al. |
| 7,081,560 B1 | 7/2006 | Lim et al. |
| 7,086,399 B2 | 8/2006 | Makinson et al. |
| 7,096,864 B1 | 8/2006 | Mayer et al. |
| 7,106,955 B2 | 9/2006 | Thudor et al. |
| 7,111,624 B2 | 9/2006 | Thudor et al. |
| 7,137,388 B2 | 11/2006 | Virr et al. |

(56) References Cited

U.S. PATENT DOCUMENTS

| | | |
|---|---|---|
| 7,140,367 B2 | 11/2006 | White et al. |
| 7,146,979 B2 | 12/2006 | Seakins et al. |
| 7,159,587 B2 | 1/2007 | Drew et al. |
| 7,228,859 B2 | 6/2007 | Loescher |
| 7,237,770 B2 | 7/2007 | Lipscombe et al. |
| 7,250,035 B1 | 7/2007 | Ott et al. |
| 7,314,046 B2 | 1/2008 | Schroeder et al. |
| 7,329,038 B2 | 2/2008 | Hashiba |
| 7,331,342 B2* | 2/2008 | Spearman ............ B01D 53/229 128/203.14 |
| 7,380,774 B2 | 6/2008 | Akita et al. |
| 7,428,902 B2 | 9/2008 | Du et al. |
| 7,487,772 B2 | 2/2009 | Ging et al. |
| 7,493,902 B2 | 2/2009 | White et al. |
| 7,571,725 B2 | 8/2009 | Wickham et al. |
| 7,614,398 B2 | 11/2009 | Virr et al. |
| 7,708,013 B2 | 5/2010 | Niland et al. |
| 7,743,767 B2 | 6/2010 | Ging et al. |
| 7,802,571 B2 | 9/2010 | Tehrani |
| 7,849,852 B2 | 12/2010 | Bremner et al. |
| 7,938,112 B2 | 5/2011 | Mayer et al. |
| 7,997,267 B2 | 8/2011 | Ging et al. |
| 8,006,691 B2 | 8/2011 | Kenyon et al. |
| 8,015,971 B2 | 9/2011 | Kwok |
| 8,020,551 B2 | 9/2011 | Virr et al. |
| 8,091,546 B2 | 1/2012 | Mantell |
| 8,194,944 B2 | 6/2012 | Tvig et al. |
| 8,240,306 B2 | 8/2012 | Cortez, Jr. et al. |
| D671,206 S | 11/2012 | McGarrity et al. |
| 8,333,195 B2 | 12/2012 | Cortez, Jr. et al. |
| 8,434,481 B2 | 5/2013 | Ogilvie et al. |
| 8,434,483 B2 | 5/2013 | Patel et al. |
| 8,434,484 B2 | 5/2013 | Patel et al. |
| 8,434,523 B2 | 5/2013 | Suhamo |
| RE44,453 E | 8/2013 | Virr et al. |
| 8,726,901 B2 | 5/2014 | Jassell et al. |
| 8,801,619 B2 | 8/2014 | Baker, Jr. et al. |
| 8,905,023 B2 | 12/2014 | Niland et al. |
| 9,072,860 B2 | 7/2015 | Lithgow et al. |
| 10,007,238 B1 | 6/2018 | Taube |
| 10,596,345 B2* | 3/2020 | Leonard ............ A61M 16/0003 |
| 2001/0035185 A1 | 11/2001 | Christopher |
| 2001/0050080 A1* | 12/2001 | Seakins ............... A61M 16/109 128/204.22 |
| 2001/0054422 A1 | 12/2001 | Smith et al. |
| 2001/0056258 A1 | 12/2001 | Evans |
| 2002/0000225 A1 | 1/2002 | Schuler et al. |
| 2002/0017302 A1 | 2/2002 | Fukunaga et al. |
| 2002/0148471 A1 | 10/2002 | Hirabayashi |
| 2002/0195104 A1 | 12/2002 | Fini et al. |
| 2003/0013980 A1 | 1/2003 | Starr et al. |
| 2003/0098022 A1 | 5/2003 | Nakao et al. |
| 2003/0211244 A1 | 11/2003 | Li et al. |
| 2003/0216285 A1 | 11/2003 | Dumont et al. |
| 2003/0236015 A1 | 12/2003 | Edirisuriya et al. |
| 2004/0016432 A1 | 1/2004 | Genger et al. |
| 2004/0050386 A1 | 3/2004 | Levine |
| 2004/0054261 A1 | 3/2004 | Kamataki et al. |
| 2004/0055597 A1 | 3/2004 | Virr et al. |
| 2004/0084046 A1 | 5/2004 | Halperin |
| 2004/0230108 A1 | 11/2004 | Melker et al. |
| 2004/0234254 A1 | 11/2004 | Czupich et al. |
| 2004/0245658 A1* | 12/2004 | Niland .................. A61M 16/16 261/DIG. 65 |
| 2005/0022828 A1 | 2/2005 | Fukunaga et al. |
| 2005/0051168 A1 | 3/2005 | DeVries et al. |
| 2005/0109340 A1 | 5/2005 | Tehrani |
| 2005/0166915 A1 | 8/2005 | Gibertoni |
| 2005/0166917 A1* | 8/2005 | Ahlmen ............... A61M 16/107 128/201.13 |
| 2005/0169615 A1 | 8/2005 | Glucksman |
| 2005/0178383 A1 | 8/2005 | Mackie et al. |
| 2005/0222503 A1 | 10/2005 | Dunlop et al. |
| 2005/0247311 A1 | 11/2005 | Vacchiano et al. |
| 2006/0021615 A1 | 2/2006 | Kertzman |
| 2006/0037613 A1 | 2/2006 | Kwok et al. |
| 2006/0055069 A1 | 3/2006 | DiMatteo et al. |
| 2006/0113690 A1 | 6/2006 | Huddart et al. |
| 2006/0118111 A1 | 6/2006 | Pelerossi et al. |
| 2006/0130836 A1 | 6/2006 | Wixey et al. |
| 2006/0184096 A1 | 8/2006 | Ott et al. |
| 2006/0191531 A1 | 8/2006 | Mayer et al. |
| 2006/0213515 A1 | 9/2006 | Bremner et al. |
| 2006/0219243 A1 | 10/2006 | Walstrom |
| 2006/0243804 A1 | 11/2006 | Christoffersen et al. |
| 2006/0272639 A1 | 12/2006 | Makinson et al. |
| 2007/0137107 A1 | 6/2007 | Barnicki |
| 2007/0137646 A1 | 6/2007 | Weinstein et al. |
| 2007/0169776 A1 | 7/2007 | Kepler et al. |
| 2007/0175473 A1 | 8/2007 | Lewis et al. |
| 2007/0283958 A1 | 12/2007 | Naghavi |
| 2008/0072899 A1 | 3/2008 | Niland |
| 2008/0078386 A1 | 4/2008 | Feldhahn et al. |
| 2008/0156328 A1 | 7/2008 | Taube |
| 2008/0183057 A1 | 7/2008 | Taube |
| 2009/0056712 A1 | 3/2009 | Cortez, Jr. et al. |
| 2009/0090363 A1 | 4/2009 | Niland et al. |
| 2009/0305214 A1 | 12/2009 | Pybus et al. |
| 2010/0059053 A1 | 3/2010 | Niland |
| 2010/0133292 A1 | 6/2010 | Ware et al. |
| 2010/0175695 A1 | 7/2010 | Jamison |
| 2010/0224191 A1 | 9/2010 | Dixon et al. |
| 2011/0152648 A1 | 6/2011 | Rustick |
| 2011/0155132 A1 | 6/2011 | Virr et al. |
| 2011/0190611 A1 | 8/2011 | Rabi |
| 2011/0200392 A1 | 8/2011 | Moncrief et al. |
| 2011/0319783 A1 | 12/2011 | Lindholt et al. |
| 2012/0016219 A1 | 1/2012 | Fujii |
| 2012/0090611 A1 | 4/2012 | Graboi et al. |
| 2012/0325207 A1 | 12/2012 | Fromage |
| 2013/0030267 A1 | 1/2013 | Lisogurski et al. |
| 2013/0174841 A1 | 7/2013 | McAuley et al. |
| 2013/0199524 A1* | 8/2013 | Hardin ............... A61M 16/0875 128/202.27 |
| 2013/0263855 A1 | 10/2013 | Tivig |
| 2013/0276780 A1 | 10/2013 | Tobia et al. |
| 2014/0166005 A1 | 6/2014 | Tatkov et al. |
| 2015/0059754 A1 | 3/2015 | Chbat et al. |
| 2015/0107588 A1 | 4/2015 | Cheung et al. |
| 2015/0306333 A1 | 10/2015 | Amadio et al. |
| 2015/0320953 A1 | 11/2015 | Acker et al. |
| 2016/0121063 A1 | 5/2016 | Tatkov et al. |
| 2016/0193438 A1 | 7/2016 | White et al. |
| 2016/0361508 A1 | 12/2016 | Cohen |
| 2017/0143538 A1 | 5/2017 | Lee et al. |
| 2019/0038865 A1 | 2/2019 | Smith et al. |
| 2020/0170513 A1 | 6/2020 | Walker |

FOREIGN PATENT DOCUMENTS

| | | |
|---|---|---|
| CA | 2617228 A1 | 9/2001 |
| CA | 2545570 | 6/2005 |
| CA | 2622734 A1 | 6/2007 |
| CA | 2691377 | 1/2009 |
| CA | 2827253 | 9/2012 |
| DE | 2843756 A1 | 4/1980 |
| DE | 10317268 A1 | 11/2004 |
| EP | 1138340 A2 | 10/2001 |
| EP | 2613840 A1 | 7/2013 |
| EP | 2608836 B1 | 3/2018 |
| EP | 3050589 B1 | 4/2020 |
| GB | 1448473 A | 9/1976 |
| GB | 2252515 A | 8/1992 |
| WO | WO-9624402 | 8/1996 |
| WO | WO-1999047197 A1 | 9/1999 |
| WO | WO-2002056931 | 7/2002 |
| WO | WO-2003035157 A1 | 5/2003 |
| WO | WO-2004096315 A2 | 11/2004 |
| WO | WO-2005038690 | 4/2005 |
| WO | WO-2005051280 | 6/2005 |
| WO | WO-2005097307 | 10/2005 |
| WO | WO-2006024292 A1 | 3/2006 |
| WO | WO-2006026387 A2 | 3/2006 |

(56) References Cited

FOREIGN PATENT DOCUMENTS

| WO | WO-2007038152 A2 | 4/2007 |
|---|---|---|
| WO | WO-2010009811 A1 | 1/2010 |
| WO | WO-2012031315 A1 | 3/2012 |

OTHER PUBLICATIONS

Partial International Search Report for International Application No. PCT/US2007/021469 dated Jul. 10, 2008.
International Search Report for Application No. PCT/US2015/067146 dated Oct. 13, 2016 (20 pages).
Supplementary Partial European Search Report dated Jan. 27, 2015 for European Application No. EP08780252.6.
International Search Report and Written Opinion for International Application No. PCT/US2008/008792 mailed on Dec. 18, 2008.
Doshi et al., "High-Velocity Nasal Insufflation in the Treatment of Respiratory Failure: A Randomized Clinical Trial", Annals of Emergency Medicine, Jul. 2017;72(1):73-83.
Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).
Adawy, et al., "Design of Fuzzy Controller for Supplying Oxygen in Sub-acute Respiratory Illnesses", IJCSI, vol. 9, Issue 3, No. 1, May 2012.
Alkurawy, "Design of an Efficient Controller for Arterial Oxygen Saturation in Neonatal Infants", PhD Thesis, University of Missouri-Columbia, Dec. 2013.
Anon., "Analog Dialogue: Pulse Oximeter", Analog Devices, Inc., 1995-2014.
Anon., "Critical Care Therapy and Respiratory Care Section", National Institutes of Health, 1112000.
Anon., "Oxygen Saturation", date unknown, downloaded Aug. 20, 2014.
Anon., "MR850 Respiratory Humidifier", Fisher & Paykel, REF 185042343, Rev. J, Aug. 2012.
Ardizzoni, "The incredible versatile op amp in medical apps", Analog devices, Nov. 2, 2009.
Branson, et al., "Is Humidification Always Necessary During Non-invasive Ventilation in the Hospital?", Respiratory Care, vol. 55, No. 2, Feb. 2010.
Carter, et al., "Evaluation of heliox in children hospitalized with acute severe asthma. A randomized crossover trial", Abstract, Chest, 109(5):1256-61, May 1996.
Davies, et al., "Inspired Gas Temperature in Ventilated Neonates", Pediatric Pulmonology 38:50-54, 2004.
Elleau, et al., "Helium-Oxygen mixture in respiratory distress syndrome: a double blind study", J Pediatr., 122 1): 132-6, Abstract, Jan. 1993.
Head et al., ES 2267141, "Treatment of a hemoglobinopatia" (translation), Mar. 1, 2007, 18 pgs.
International Preliminary Report on Patentability for PCT Patent Application No. PCT/US2020/057823, dated May 10, 2022, 9 pages.
International Preliminary Report on Patentability for PCT Patent Application No. PCT/US2020/062118, dated May 17, 2022, 6 pages.
International Search Report and Written Opinion in International application No. PCT/US2020/057823 dated Jan. 28, 2021.
International Search Report and Written Opinion in International application No. PCT/US2020/062118 dated Mar. 11. 2021.
Kass, et al., "Heliox therapy in acute severe asthma", Abstract, Chest, 107(3):757-60, Mar. 1995.
Kudukis, et al., "Inhaled helium-oxygen revisited: effect of inhaled helium-oxygen during the treatment of status asthmaticus in children", Abstract, J Pediatr., 130(2):217-24, Feb. 1997.
Lu, et al., "Helium-Oxygen in Treatment of Upper Airway Obstruction", Anesthesiology, vol. 45, Dec. 1976.
Manthous, et al., "Heliox improves pulsus paradoxus and peak expiratory flow in nonintubated patients with severe asthma", AM J Respir Grit Care Med. Abstract, 151(2pt 1):310-4, Feb. 1995.
Martin-Barbaz, et al., "Use of helium oxygen mixtures in status asthmaticus", Abstract, Rev Pneumol Clin. 43 4):186-9, 1987.
Panchal, et al., "Feedback-Controlled System to Titrate Oxygen Delivery", Drexel University, Winter 014, 41 pages.
Sano, et al., Adaptive control of arterial oxygen pressure of newborn infants under incubator oxygen treatments, IEE Proceeding, vol. 132, Pt. D., No. 5, Sep. 1985.
Sauder, et al., "Helium-oxygen and conventional mechanical ventilation in the treatment of large airway obstruction and respiratory failure in an infant", Abstract, South Med J_84(5):646-8, May 1991.
Shiue, et al., "The use of helium-oxygen mixtures in the support of patients with status asthmaticus and respiratory acidosis", J Asthma, Abstract, 26(3):177-80, 1989.
Soto, et al., "Automatic Ventilation Control", Freescale.com/beyondbits, undated, downloaded Sep. 17, 2014.
Swidwa, et al., "Helium-oxygen breathing in severe chronic obstructive pulmonary disease", Abstract, Chest, 9=87 6):790-5, Jun. 1985.
Wolfson, et al., "Mechanics and energetics of breathing helium in infants with bronchopulmonary dysplasia", Abstract, J Pediatr., 104(5):752-7, May 1984.

* cited by examiner

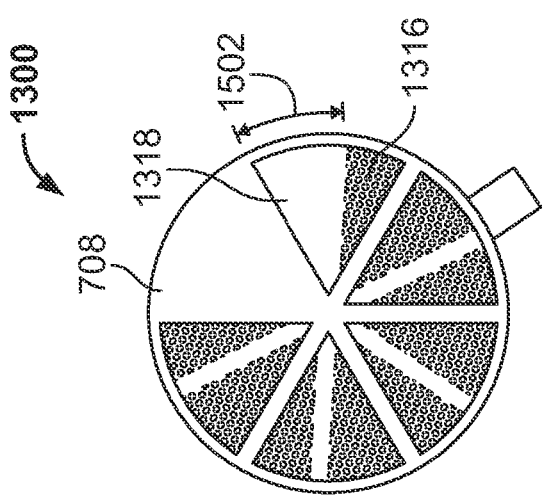
FIG. 12
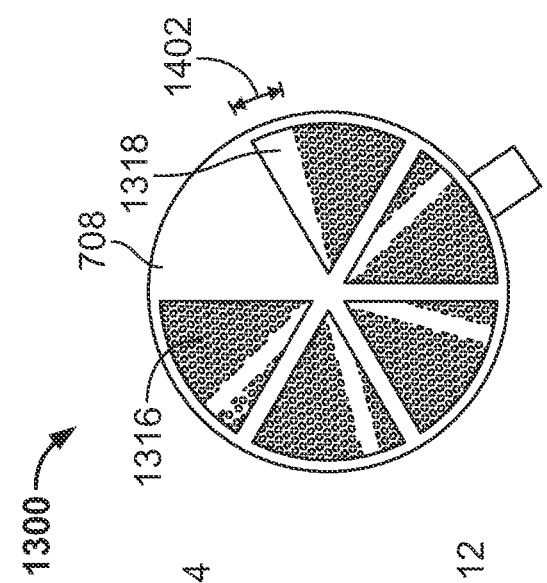
FIG. 13
FIG. 14
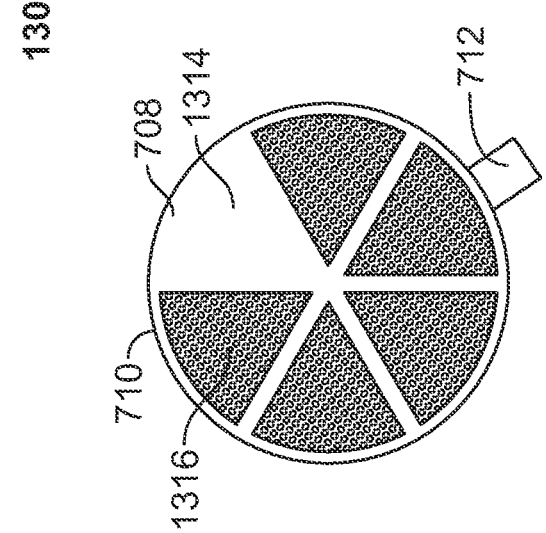
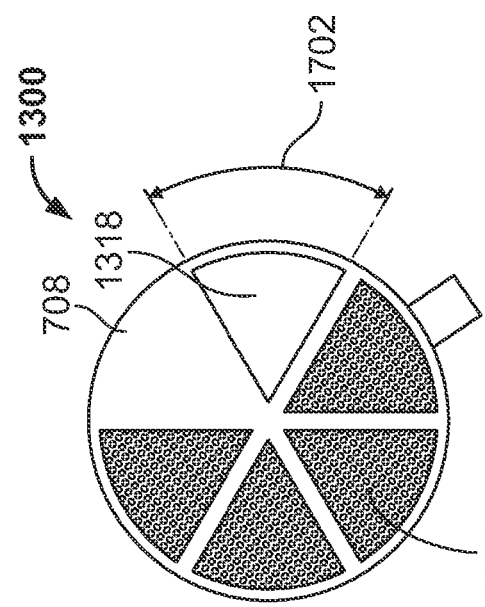
FIG. 15
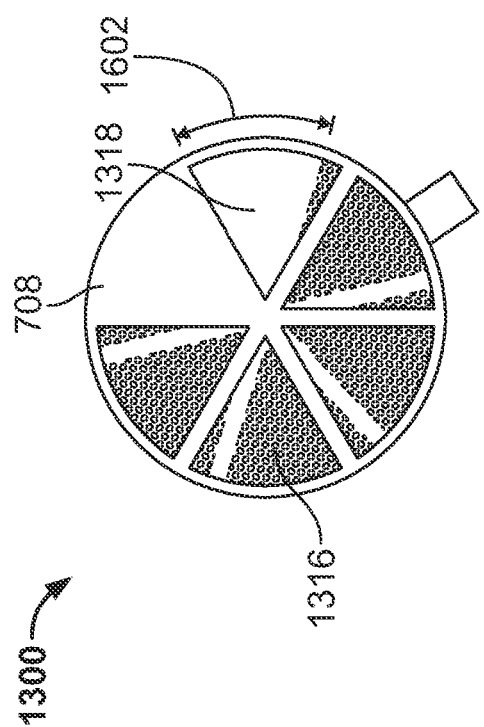
FIG. 16

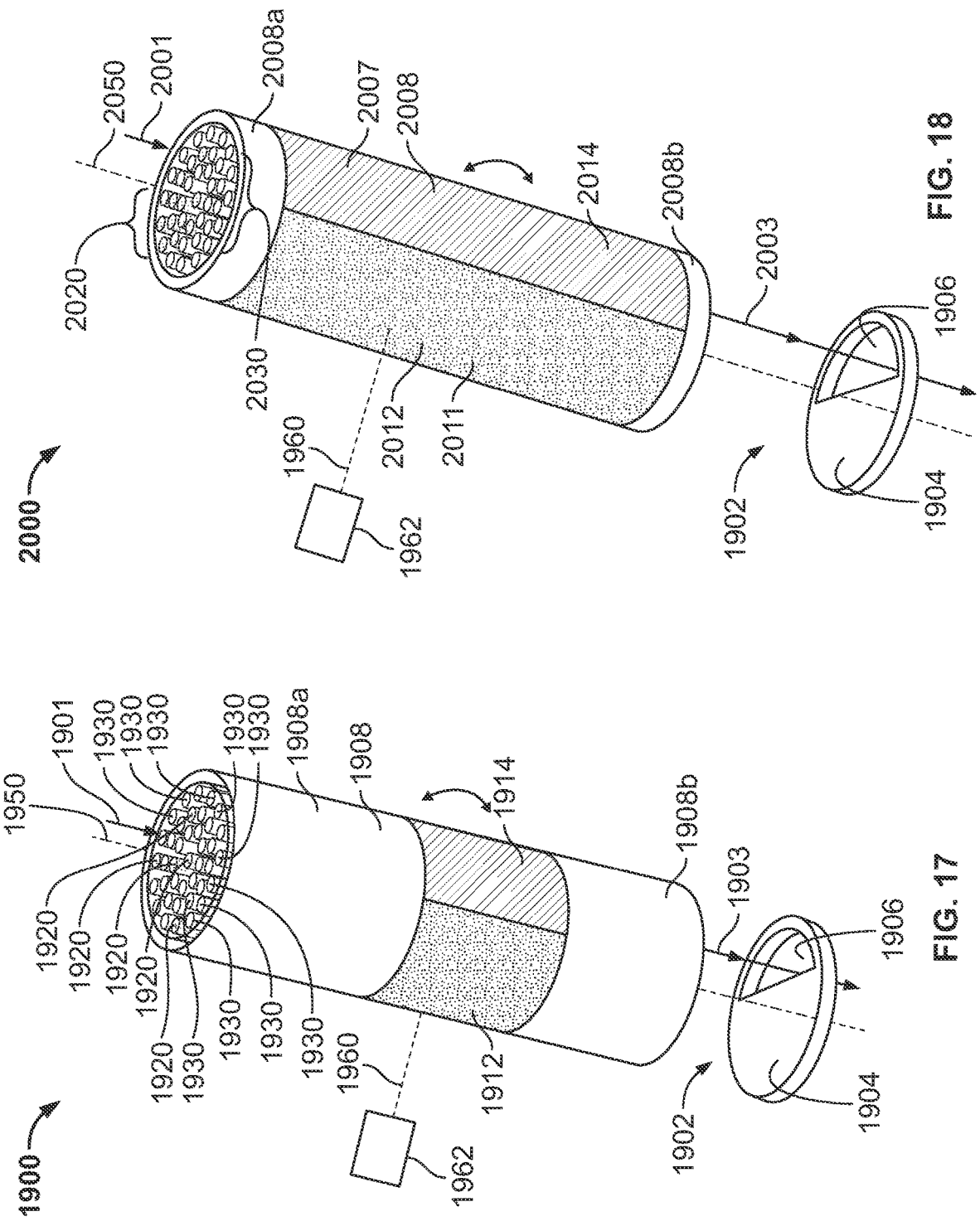

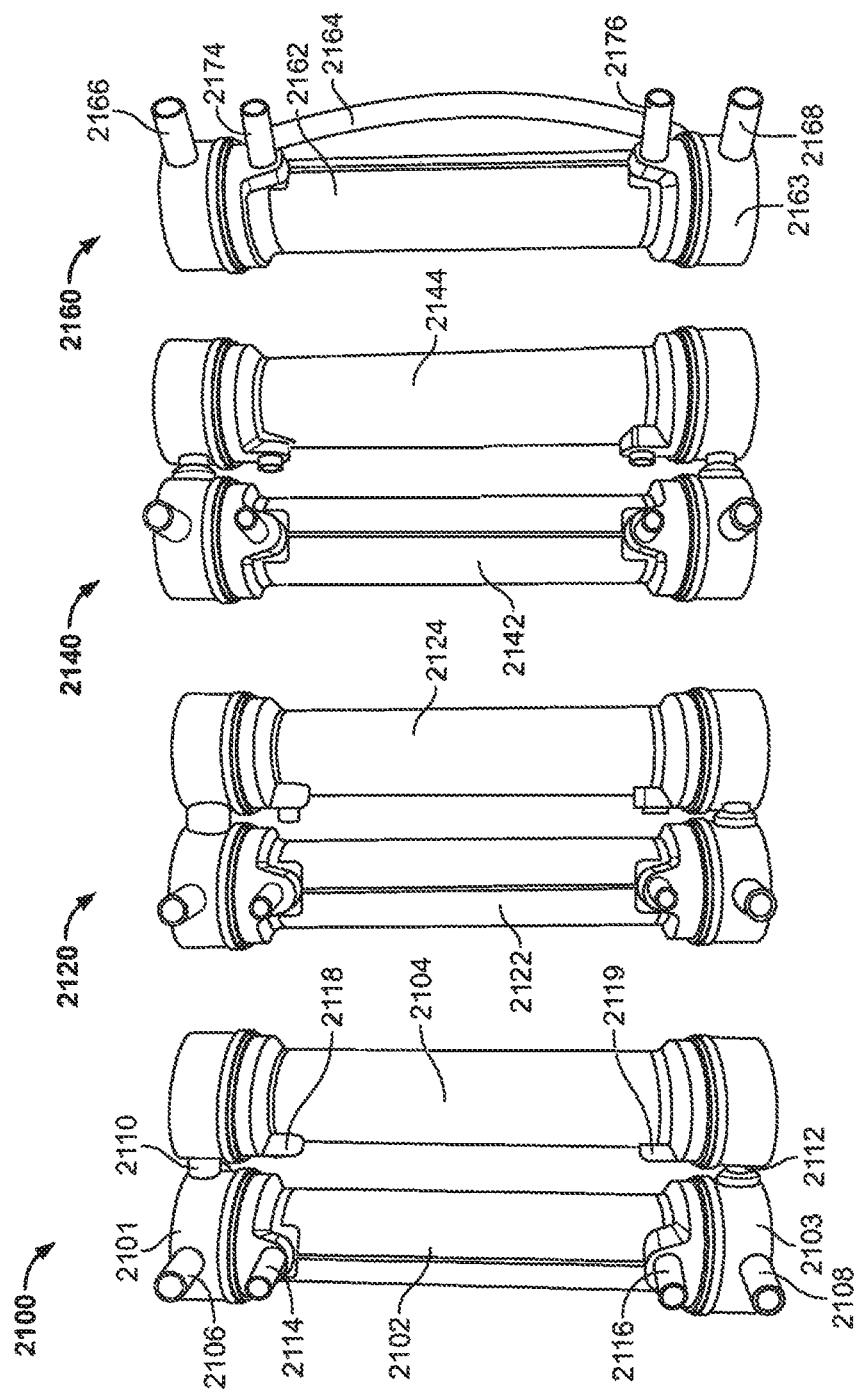

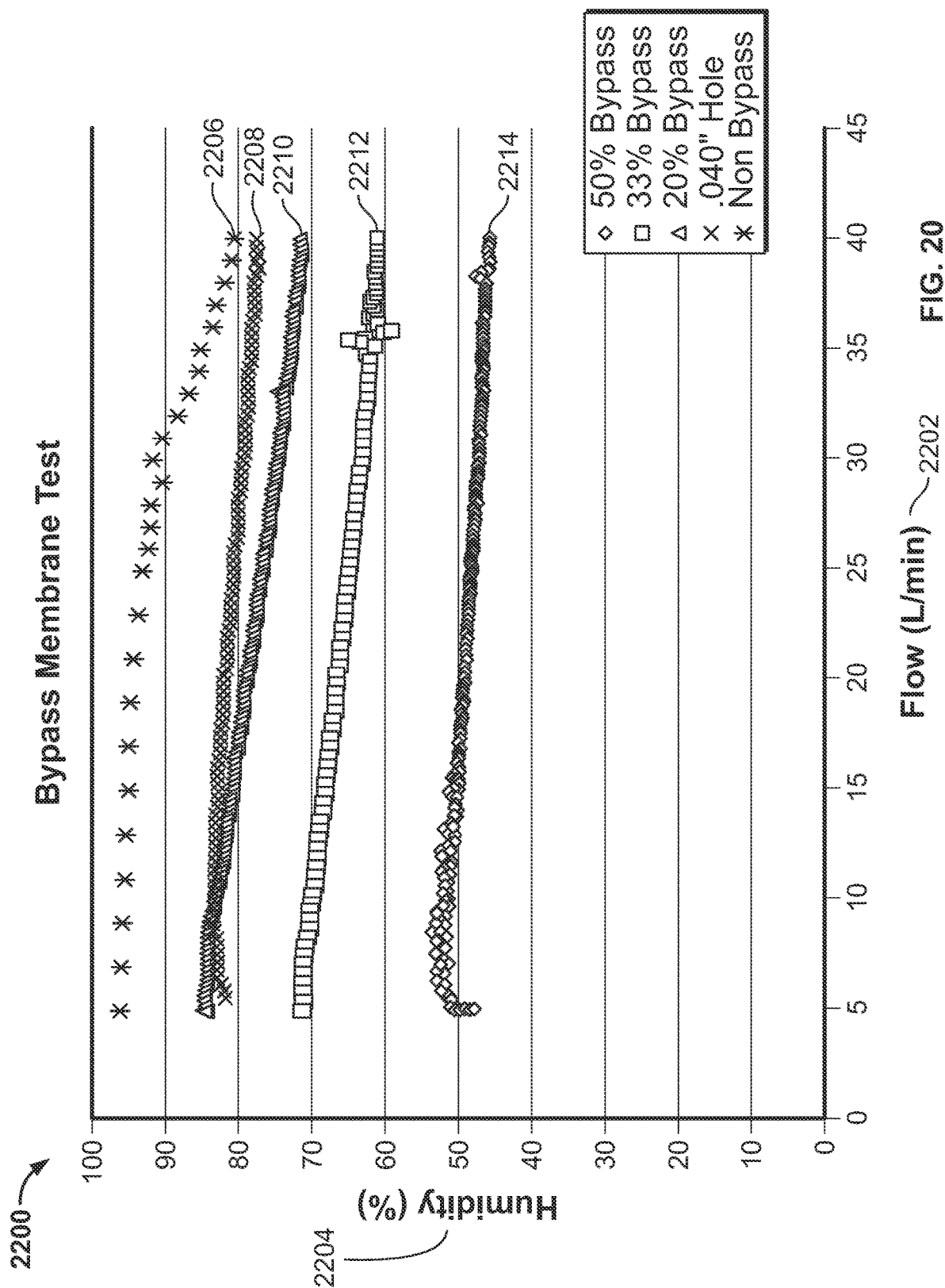

SYSTEMS AND METHODS FOR HUMIDITY CONTROL

CROSS-REFERENCE TO RELATED APPLICATIONS

This application is a divisional of U.S. patent application Ser. No. 14/587,898 filed on Dec. 31, 2014 (now U.S. Pat. No. 10,596,345). The foregoing applications is hereby incorporated by reference in its entirety

BACKGROUND

Patients with respiratory ailments are often treated with respiratory assist devices that deliver supplemental breathing gas to a patient. Such devices may deliver gas to a patient using high flow therapy (HFT). HFT devices deliver breathing gas to a patient at a high flow rate via an interface such as a nasal cannula to increase the patient's fraction of inspired oxygen (FiO2), decrease a patient's work of breathing, or do both. That helps the patient recover from respiratory ailments, such as respiratory distress or bronchospasms. Some HFT devices heat and humidify the delivered breathing gas for medical reasons (e.g., to maintain the pliability of the tissues of surfactant-deficient patients, or to preserve mucosal integrity) or to reduce patient discomfort.

A challenge associated with delivering breathing gas via a high-flow system is condensation of moisture from the heated and humidified breathing gas. Condensation in a ventilation circuit presents both clinical and mechanical challenges. The condensate can accumulate in the gas circuit and thus limit flow through the system. Movement of accumulated condensate liquid in the gas circuit into the patient can present a risk of aspiration. Additionally, the condensate can collect and stagnate, posing a biologic hazard to the patient.

In many devices that provide humidified breathing gas, gas flow rates can become sufficiently low that the gas passing through the device spends more time in the humidification region. As a result, the humidity level of the gas flow exiting the device toward the patient can approach 100% relative humidity. When the humidified gas cools at the patient interface, its humidity will condense and form liquid droplets in the tube carrying the gas. This unwanted condensation becomes more problematic at the lower flow rates where humidification can approach 100% relative humidity. The liquid droplets could pose health risks if they were allowed to stagnate because they could facilitate the growth of harmful microorganisms. Also, the liquid droplets could accumulate and impede the gas flow or even be delivered to a patient's respiratory tract, potentially causing discomfort or other health problems. On the other hand, increasing the flow rate of a humidification device can detrimentally reduce the humidification of the gas, impeding the benefits of humidified breathing gas. Dry breathing gas can cause patient discomfort at high flow rates because dry gas can dry the patient's airway. A complication is that vapor transfer systems that are configured to deliver humidified breathing gas at high flow rates can cause excessive condensation to occur at low flow rates.

One solution is to provide separate, dedicated vapor transfer units, one for operating at high flow rates and another for operating at low flow rates. The use of separate vapor transfer units complicates the use of high flow therapy systems by requiring a healthcare professional to turn off the system and switch vapor transfer units. The switching of vapor transfer units can also interrupt a patient's therapy.

SUMMARY

Systems, methods, and devices for humidifying a breathing gas using a vapor transfer unit are presented. In one aspect, a method provides a first vapor transfer unit having a gas passage and a liquid passage, delivering a liquid to the liquid passage, delivering a gas to the gas passage, humidifying the gas by delivering vapor from the liquid in the liquid passage to the gas in the gas passage, exiting the humidified gas outside the vapor transfer unit at first relative humidity and at a high gas flow rate, and reducing the gas flow rate through the first vapor transfer unit to less than a low gas flow rate, while preventing the relative humidity from exceeding the first relative humidity by more than an acceptable margin. Acceptable margins can be pre-established and pre-programmed into the vapor transfer unit control system, and may include an indicator that indicates when the margin is exceeded. Acceptable margins may include about 10% relative humidity or less. The margin may be about 8%, 6%, 4%, or less. In some implementations, the method also includes passing a fraction of the gas through a bypass passage parallel to the gas passage and automatically altering the fraction of the gas passed through the bypass passage inversely with a change in the gas flow rate. The method may also include obstructing gas flow through a portion of the gas passage and adjusting the relative humidity by changing the portion of the gas passage that is obstructed.

The systems, devices, and methods disclosed herein control the humidity of a breathing gas over a range of flow rates. The systems, devices and methods impede or prevent excessive humidification of a breathing gas at low gas flow rates while impeding or preventing a significant drop in humidity at high flow rates (e.g., >8 L/min, >10 L/min, >15 L/min, >20 L/min, >30 L/min, >35 L/min, or another similar flow rate). This is done using a vapor transfer unit. At low flow rates (e.g., >30 L/min, >20 L/min, >15 L/min, >10 L/min, >8 L/min, or another similar flow rate), gas flowing through the vapor transfer unit has more time to receive humidity than at high flow rates. Therefore, the systems, devices, and methods disclosed herein limit the humidity of breathing gasses at low flow rates. This can be done in various ways. The humidity can be limited by allowing a fraction of input gas to bypass humidification. The humidity of the breathing gas can also be limited by changing the number of humidification elements exposed to the flow of the input gas or by changing the number of humidification elements exposed to the flow of liquid. At high flow rates, gas flowing through a vapor transfer unit has less time to receive vapor and be humidified, so there is a greater risk of inadequate humidification at high flow rates. Therefore, at high flow rates, the systems, devices and methods disclosed herein preferably also maintain the relative humidity of the output gas at a desired relative humidity level. By enabling a single vapor transfer unit to perform at both high and low flow rates, the systems, devices, and methods, can eliminate the need for switching vapor transfer units when flow rates are altered between high and low flow.

In some implementations, a bypass passage is used to vary the humidification. The bypass passage automatically admits a smaller fraction of incoming gas in response to an increase in flow rate. The bypass passage may be valve controlled or not. In certain implementations, a valve is manipulated to select the fraction of gas that bypasses humidification or to select the total number of humidification elements exposed to gas flow, or both. In some implementations, humidification is controlled by varying the amount of liquid allowed to pass through the humidification elements by controlling the flow rate, or by a valve, or both. In a preferred implementation, the humidity control system is used with high flow therapy (HFT). Nevertheless, the humidity control system may also be used with other types of respiratory therapy and respiratory therapy devices, including low flow oxygen therapy, continuous positive airway pressure therapy (CPAP), mechanical ventilation, oxygen masks, Venturi masks, and tracheotomy masks, to name a few.

In one aspect, systems and devices are provided that achieve controlled humidification through a vapor transfer unit. In embodiments, a vapor transfer unit for humidifying breathing gas includes a housing having a gas inlet and a gas outlet, a plurality of tubes disposed within the housing and each defining a passage for a flow of gas from an upstream end of the passage to a downstream end of the passage, and a valve positionable between a first position and a second position. The valve obstructs the flow of gas through a first subset of the plurality of tubes when in the first position, and the valve obstructs the flow of gas through a second subset of the plurality of tubes, different from the first set, when in the second position. In some implementations, the plurality of tubes comprises a first group and a second group, wherein tubes of the first group are porous and tubes of the second group are non-porous. The first position may correspond to a first ratio of unobstructed porous tubes to unobstructed non-porous tubes, and the second position may correspond to a second ratio of unobstructed porous tubes to unobstructed non-porous tubes. In some implementations, the first ratio is greater than the second ratio. In certain implementations, the first ratio is greater than about 50 and the second ratio is less than about 25. In some implementations, a first number of tubes included in the first subset is greater than a second number of tubes included in the second subset.

In certain implementations, the valve is positionable at a plurality of intermediate positions, wherein the plurality of intermediate positions are between the first and second positions. The gas inlet may be positioned to direct gas to the upstream end of each of the passages of the tubes, and the gas outlet may be positioned to direct gas from the downstream end of each of the passages of the tubes. In some implementations, the housing includes a liquid inlet positioned to direct liquid toward outer surfaces of the tubes and a liquid outlet positioned to direct liquid from the housing. In certain implementations, the tubes include a first group and a second group, wherein tubes of the first and second groups are porous. In some implementations, the second group of tubes is configured to prevent liquid from contacting outer surfaces of tubes of the second group.

According to another aspect, methods are provided for humidifying a breathing gas using a vapor transfer unit. In embodiments, the methods include delivering gas to a plurality of tubes disposed within a housing, directing liquid toward outer surfaces of the plurality of tubes, obstructing gas flow through a subset of the plurality of tubes, and adjusting a humidity level of gas output from the vapor transfer unit by adjusting the subset of obstructed tubes so that different tubes are obstructed. For example, increasing the number of tubes that are obstructed can lower the humidity level of the gas output, while decreasing the number of obstructed tubes can increase the humidity level of the gas output. In some implementations, a first group of the tubes are porous and a second group of the tubes are non-porous. In certain implementations, the plurality of tubes comprises a number of unobstructed porous tubes and a number of unobstructed non-porous tubes, and adjusting the subset of obstructed tubes includes changing a ratio of the number of unobstructed porous tubes to the number of unobstructed non-porous tubes from a first ratio to a second ratio. In some implementations, the first ratio is greater than about 50 and the second ratio is less than about 25. In certain implementations, the first ratio is about 75, 100, 200, 500, or any other suitable number. In some implementations, the second ratio is about 20, 10, 8, 6, 4, 2, or any other suitable number. In certain implementations, adjusting the subset of obstructed tubes includes changing a total number of obstructed tubes so there are more or fewer obstructed tubes. In some implementations, the gas is delivered at a flow rate of greater than 8 liters per minute. In certain implementations, liquid is directed to outer surfaces of a first group of the plurality of tubes and is not directed to outer surfaces of a second group of the plurality of tubes.

According to another aspect, systems and devices are provided to control humidification. In embodiments, a vapor transfer unit for humidifying breathing gas includes a housing, a vapor transfer compartment, and a bypass gas passage. The housing includes a liquid inlet, a liquid outlet, a gas inlet, and a gas outlet. The vapor transfer compartment is disposed within the housing and includes a first gas passage coupling the gas inlet to the gas outlet, a liquid passage coupling the liquid inlet to the liquid outlet, and a porous membrane separating the first gas passage and the liquid passage. The bypass gas passage is disposed within the housing and couples the gas inlet to the gas outlet. The bypass gas passage includes a constriction and is configured to receive a fraction of the gas received by the gas inlet. The constriction is sized so that the fraction of gas received by the bypass passage decreases as a rate of gas flow into the gas inlet increases. In some implementations, a cross-sectional area of the constriction is fixed. In certain implementations, the porous membrane comprises a plurality of hollow fiber membranes. In some implementations, the first gas passage is defined by internal walls of the plurality of hollow fiber membranes. In certain implementations, the liquid inlet is formed in the housing and is positioned to direct liquid toward outer surfaces of the hollow fiber membranes and the liquid outlet is positioned to direct liquid from the housing.

According to another aspect, methods for humidifying a breathing gas using a vapor transfer unit include delivering gas to a vapor transfer unit having a vapor transfer device and a bypass gas passage, wherein the gas is delivered at a gas flow rate, passing a fraction of the gas through the bypass gas passage, and automatically altering the fraction of the gas passed through the bypass gas passage inversely with a change in the gas flow rate. The method may also include maintaining fixed internal dimensions of the vapor transfer unit. In certain implementations, passing the fraction of the gas through the bypass gas passage includes passing gas through a constriction, wherein the constriction is sized so that the fraction of gas received by the bypass gas passage decreases as the gas flow rate increases.

In some implementations, the methods include delivering liquid to the vapor transfer device. In certain implementations, the vapor transfer device includes a first gas passage and a liquid passage, where the gas is delivered to the first gas passage and the liquid is delivered to the liquid passage. The vapor transfer device may include a plurality of hollow fiber membranes. In certain implementations, delivering the liquid comprises directing liquid toward outer surfaces of the plurality of hollow fiber membranes. In some implementations, the gas is delivered at a high flow rate. The gas may be delivered at a flow rate of >8 L/min, >10 L/min, >20 L/min, >30 L/min, >35 L/min, or at any other suitable flow rate.

Methods are also provided for humidifying a breathing gas using a vapor transfer unit. The methods include providing a first vapor transfer unit having a gas passage and a liquid passage, delivering a liquid to the liquid passage, delivering a gas to the gas passage, humidifying the gas by delivering vapor from the liquid in the liquid passage to the gas in the gas passage, exiting the humidified gas outside the vapor transfer unit at a first relative humidity and at a gas flow rate greater than about 35 liters per minute, and reducing the gas flow rate through the first vapor transfer unit to less than about 20 liters per minute, while preventing the relative humidity of the humidified gas exiting the vapor transfer unit from exceeding the first relative humidity by more than a specified margin, wherein the margin is about 10% relative humidity or less. The margin may be 8%, 6%, 4%, or any other suitable margin.

In some implementations, methods also include passing a fraction of the gas through a bypass passage parallel to the gas passage. In certain implementations, the methods include automatically altering the fraction of the gas passed through the bypass passage inversely with a change in the gas flow rate. As the flow rate increases, a smaller fraction of the gas is passed through the bypass passage, whereas a larger fraction of the gas is passed through the bypass passage when the flow rate decreases. In some implementations, the methods include obstructing gas flow through a portion of the gas passage and adjusting the relative humidity by changing the portion of the gas passage that is obstructed. By changing the portion of the gas passage that is obstructed, a ratio of unobstructed porous tubes to unobstructed non-porous tubes in the gas passage can be increased, therefore the relative humidity increases. Alternatively, the ratio of unobstructed porous tubes to unobstructed non-porous tubes can be decreased, therefore the relative humidity decreases. In certain implementations, delivering the gas to the gas passage further comprises delivering gas to a plurality of hollow fiber membranes disposed within the gas passage. In some implementations, delivering the liquid to the liquid passage also includes directing liquid toward outer surfaces of the plurality of hollow fiber membranes. In certain implementations, the margin is about 8% relative humidity. In some implementations, the margin is about 6% relative humidity. In certain implementations, the margin is about 4% relative humidity. In some implementations, the first relative humidity is significantly below saturation (e.g., <70%, <80%, <85%, <90%, <95%, or <99%).

According to another aspect, a vapor transfer unit for humidifying breathing gas includes a housing having a gas inlet and a gas outlet, a plurality of tubes disposed within the housing and each defining a passage for a flow of gas from an upstream end of the passage to a downstream end of the passage, and a liquid inlet positioned to direct liquid toward outer surfaces of the tubes, wherein the plurality of tubes comprises a first group of tubes and a second group of tubes and wherein tubes of the first group are porous. In some implementations, tubes of the second group are non-porous. In certain implementations, tubes of the second group are porous. In some implementations, tubes of the first group are configured to contact the liquid, and tubes of the second group are configured to be separate from the liquid. In certain implementations, a number of tubes included in the first group is greater than a number of tubes included in the second group. In some implementations, a number of tubes included in the first group is greater than or about equal to three times the number of tubes included in the second group.

A bypass passage having a constriction can be added to any of the implementations or embodiments described above. For example, a vapor transfer unit having a valve for adjusting the subset of tubes that are exposed to gas flow may also include a bypass passage having a constriction. Such a vapor transfer unit allows both automatic and manual adjustment of the output humidity. The bypass passage can be added in parallel to a vapor transfer unit or a portion of a vapor transfer unit.

Additionally, any of the implementations described above may include a subset of inactive tubes that are non-porous, isolated from liquid flow, or both. The inclusion of such inactive tubes in a vapor transfer unit allows a portion of incoming gas to bypass humidification. Flow to the inactive tubes can be constant or can be controlled by a valve, a constricted orifice, or both. If both a valve and a constricted orifice are used, the valve and constricted orifice can be used in series, in parallel, or both.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 12-16 show bottom views of a vapor transfer unit having a rotating valve;

FIG. 17 shows an exploded view of a vapor transfer unit having a rotatable housing;

FIG. 18 shows an exploded view of another vapor transfer unit having a rotatable housing;

FIGS. 19A-19D show illustrative vapor transfer units having different output humidity levels;

FIG. 20 shows a plot of relative humidity as a function of gas flow rate for the vapor transfer units of FIGS. 19A-19D;

DETAILED DESCRIPTION

To provide an overall understanding of the systems, devices, and methods described herein, certain illustrative embodiments will be described. Although the embodiments and features described herein are specifically described for use in connection with a high flow therapy system, it will be understood that all the components and other features outlined below may be combined with one another in any suitable manner and may be adapted and applied to other types of respiratory therapy and respiratory therapy devices, including mechanical ventilation, continuous positive airway pressure therapy (CPAP), oxygen masks, Venturi masks, low flow oxygen therapy, tracheotomy masks, and the like.

The systems, devices, and methods described herein control the relative humidity of a breathing gas delivered from a breathing gas humidification system. The systems, devices and methods impede or prevent excessive humidification of a breathing gas at low gas flow rates while impeding or preventing a significant drop in humidity at high flow rates using a single vapor transfer unit. In some implementations, a fraction of gas flow through a vapor transfer unit bypasses humidification. In these implementations, the fraction of gas that bypasses humidification varies inversely with the flow rate. Thus, a larger fraction of the total flow is bypassed at lower flow rates to prevent excessive humidification which could cause condensation, while a smaller fraction of the gas is bypassed at high flow rates so that humidity at high flow rates remains acceptably high for patient comfort. The fraction of total flow that is admitted to the bypass passage may be reduced automatically using a constriction in the bypass passage that is sized to admit a smaller fraction of the total flow as the flow rate increases. The bypass path may be manually controlled using a rotating or sliding valve. In some implementations, the total number of humidification elements exposed to the gas flow is varied to control the humidity level at high and low flow rates. In these implementations, more humidification elements are exposed to the flow at high flow rates, and fewer humidification elements are exposed to the flow at low flow rates. By enabling a single vapor transfer unit to perform at both high and low flow rates, the systems, devices, and methods can eliminate the need for separate vapor transfer units for high and low flow rates.

Figures 1A, 1B:
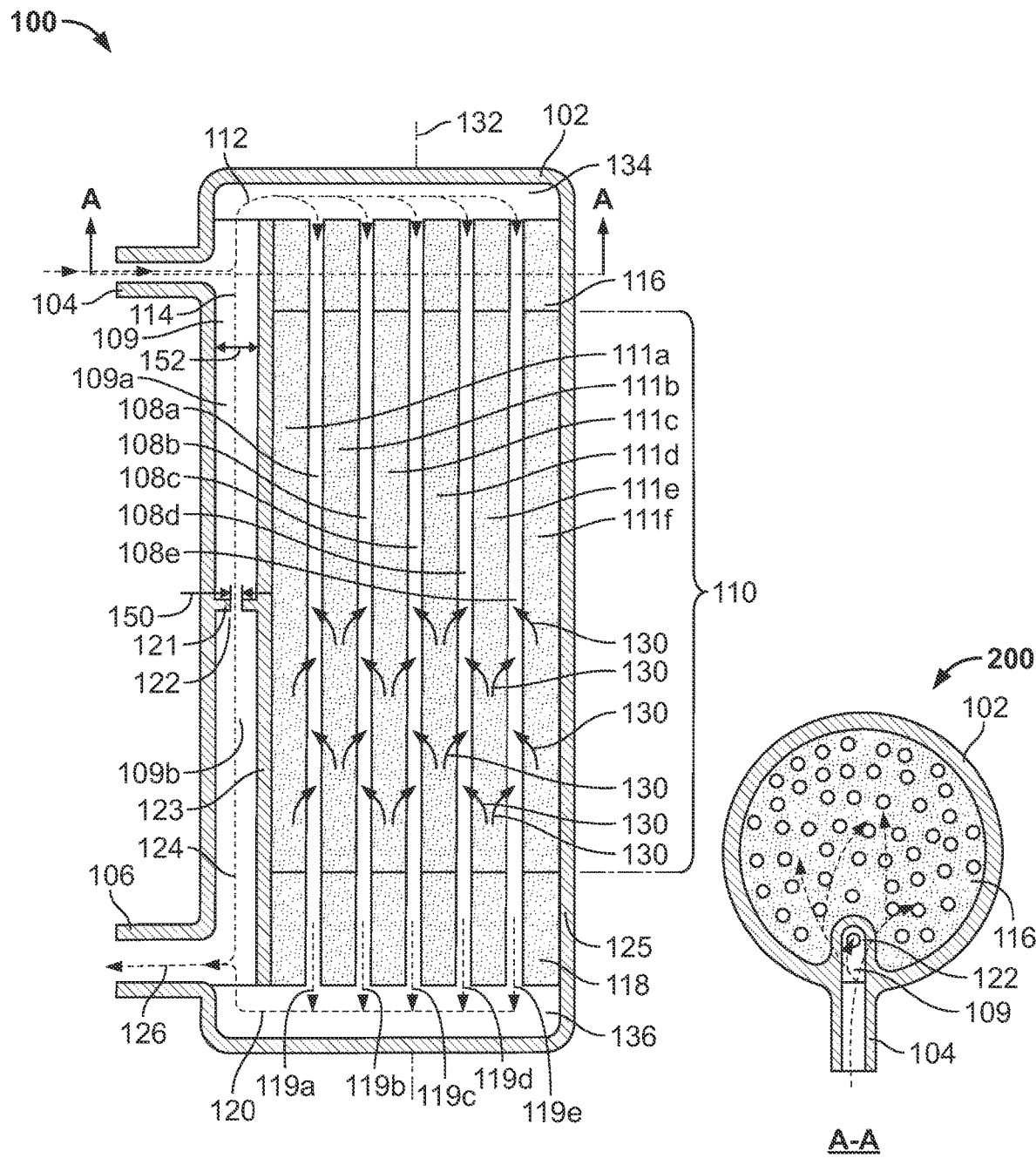
FIG. 1A shows an illustrative vapor transfer unit for humidity control.
FIG. 1B shows a cross section view of the vapor transfer unit of FIG. 1A.

FIG. 1A shows a vapor transfer unit 100 for humidity control, according to certain implementations. FIG. 1B shows a cross section view 200 of the vapor transfer unit 100. The vapor transfer unit 100 includes a housing 102 having a longitudinal axis 132, a gas inlet 104, and a gas outlet 106. The vapor transfer unit 100 also includes a plurality of tubes 108a-e disposed within the housing 102. The tubes 108a-e each define a passage for the flow of gas from the gas inlet 104 to the gas outlet 106. The tubes 108a-e may be hollow fiber membranes that are permeable to water vapor, but are impermeable or somewhat impermeable to liquid water. Gas flowing in the inlet 104 enters an upper chamber 134 and splits into the respective tubes 108a-e, where the flow occurs in parallel. The gas then combines in the bottom chamber 136 and then flows out of the gas outlet 106. Between the tubes 108a-e is a plurality of liquid regions 111a-f in which liquid circulates. The tubes 108a-e are porous so that the liquid circulating in the regions 111a-f transfers vapor to the gas passing through the tubes 108a-e as indicated by the arrows 130. Thus, the gas 112 is humidified as it travels along the humidification region 110 of the tubes 108a-e. The tubes 108a-e pass through plugs 116 and 118, and the outer surfaces of the tubes 108a-e are held by the plugs 116 and 118. The tubes 108a-e may be held by an interference fit with the holes in the plugs 116 and 118 through which the tubes 108a-e pass. In some implementations, the tubes 108a-e are bonded to the plugs 116 and 118. The plugs 116 and 118 are substantially disk-shaped and concentric to the longitudinal axis 132 of the housing 102. The plugs 116 and 118 are held in the housing 102 by walls 123 and 125. The plugs may be held by an interference fit, bonded, or welded to the walls 123 and 125, or connected to the walls 123 and 125 using any other suitable attachment, or combination thereof. The plugs 116 and 118 support the tubes 108 while also enclosing the regions 111a-f in which the liquid circulates.

The vapor transfer unit 100 also includes a bypass passage 109 that provides a passage from the gas inlet 104 to the gas outlet 106. The bypass passage includes a constriction 122 which provides resistance to the flow of gas 114 through the bypass passage 109. The constriction 122 is defined by a ring-shaped protrusion 121 that narrows the internal diameter of the bypass passage from an initial diameter 152 to a restricted diameter 150. The restricted diameter is generally sized so that the flow resistance caused by the constriction 122 increases about linearly with velocity squared. In preferred implementations, the restricted diameter is about 0.75 mm-1.5 mm. In example embodiments, the restricted diameter is about 0.040 in (1.016 mm). The protrusion 121 is located about midway between the gas inlet 104 and the gas outlet 106 and is oriented perpendicular to the longitudinal axis 132 of the housing 102 and separates an upstream portion 109a of the bypass passage 109 from a downstream portion 109b of the bypass passage 109. The protrusion 121 may be located closer to the gas inlet 104 or closer to the gas outlet 106. In certain implementations, the constriction 122 is oriented oblique to the longitudinal axis 132 of the housing 102. The protrusion 121 can be formed by fabricating a wall (not shown) to separate the upstream portion 109a of the bypass passage 109 from the downstream portion 109b of the bypass passage 109 and then drilling a small hole in the wall. The bypass passage 109 is separated from the regions 111 in which the liquid circulates by non-porous wall 123. Since the wall 123 is non-porous, vapor is not transferred from the circulating liquid into the gas 114 passing through the bypass passage 109.

The vapor transfer unit 100 is configured so that a first fraction 112 of the gas flow through the gas inlet 104 passes through the tubes 108, and a second fraction 114 of the gas flow passes though the bypass passage 109 and exits as bypassed gas 124. The fraction 112 passing through the tubes 108 is humidified in the humidification region 110, while the fraction 114 passing through the bypass passage 109 is not humidified. The first fraction 112 exits the tubes 108a-e as humidified gas 119a-e, respectively, and recombines in the bottom chamber 136 to form the humidified gas 120. The humidified gas 120 and the bypassed gas 124 combine near the outlet 106 to form an output gas 126.

As the rate of gas flow into the inlet 104 increases, the resistance to gas flow through the bypass passage 109 caused by the constriction 122 in the bypass passage 109 increases and in most cases more than the resistance to gas flow caused by the plurality of tubes 108a-e. The resistance to flow through the tubes 108a-e is mostly due to frictional drag against the walls of the tubes 108a-e, while the losses due to entrance and exit effects are relatively minor. In contrast, the resistance to flow through the constriction 122 is generally due to entrance and exit effects (e.g., losses associated with compression of the gas entering the constriction 122 and expansion of the air exiting the constriction 122). Flow resistance due to frictional drag varies linearly with velocity, while flow resistance due to entrance and exit effect increases with velocity squared. As a result, when the flow rate through the gas inlet 104 increases, the resistance of the constriction 122 increases more rapidly than the resistance of the plurality of tubes 108a-e. Thus, a greater fraction of the gas flow entering the gas inlet 104 passes through the plurality of tubes 108a-e. Conversely, when the flow rate through the gas inlet 104 decreases, the fraction 114 of gas passed through the bypass passage 109 increases relative to the fraction 112 of gas passed through the plurality of tubes 108a-e. Thus, the fraction 114 of gas passed through the bypass passage 109 varies inversely with the gas flow rate through the gas inlet 104.

The constriction 122 allows the flow rate through the gas inlet 104 to be altered without significantly changing the relative humidity of the gas 126 exiting the gas outlet 106. The gas flow 124 from the bypass passage 109 combines with the gas flow 126 before the outlet 106 to lower the relative humidity of the output gas 126 exiting the gas outlet 106 to below saturation (100% relative humidity). The combination of humidified gas 120 with bypassed gas 124 can thus lower the relative humidity of the output gas 126 to reduce the risk of unwanted condensation at low flow rates. As the flow rate through the gas inlet 104 decreases, the humidity of gas flow 120 increases, but the fraction of bypassed gas 124 also increases. Therefore the increase in humidity at low flow rates is counteracted by an increase in the fraction 114 of gas that bypasses humidification. Thus, the bypass passage 109 helps impede or prevent condensation at low flow rates (e.g., flow rates through the gas inlet 104 of <30 L/min, <20 L/min, <10 L/min, <8 L/min, <5 L/min, or any similar flow rate).

In contrast, when gas flow rates through the gas inlet 104 are high, the gas passing through the vapor transfer unit 100 spends less time in the humidification zone 110. Thus, the gas flow 120 may not approach 100% relative humidity. As a result, there is less need to mix bypassed gas 124 with the humidified gas 120 to prevent condensation at high flow rates. Due to the constriction 122, the fraction of bypassed gas 124 decreases relative to the fraction of humidified gas 120 at high flow rates. Therefore, more of the gas passing through the vapor transfer unit 100 is humidified as the flow rate increases to counteract the decrease in humidification that normally occurs at high flow rates. By varying the fraction of bypassed gas 124 inversely with the changing flow rate, the constriction 122 reduces the risk of condensation at low flow rates, while not excessively reducing the humidification at high flow rates. Furthermore, the humidity control is achieved automatically and without the need for electronic sensors, actuators, feedback control systems, or valves. Instead, the internal dimensions of the bypass passage 109 and constriction 122 remain fixed during operation.

Figure 2:
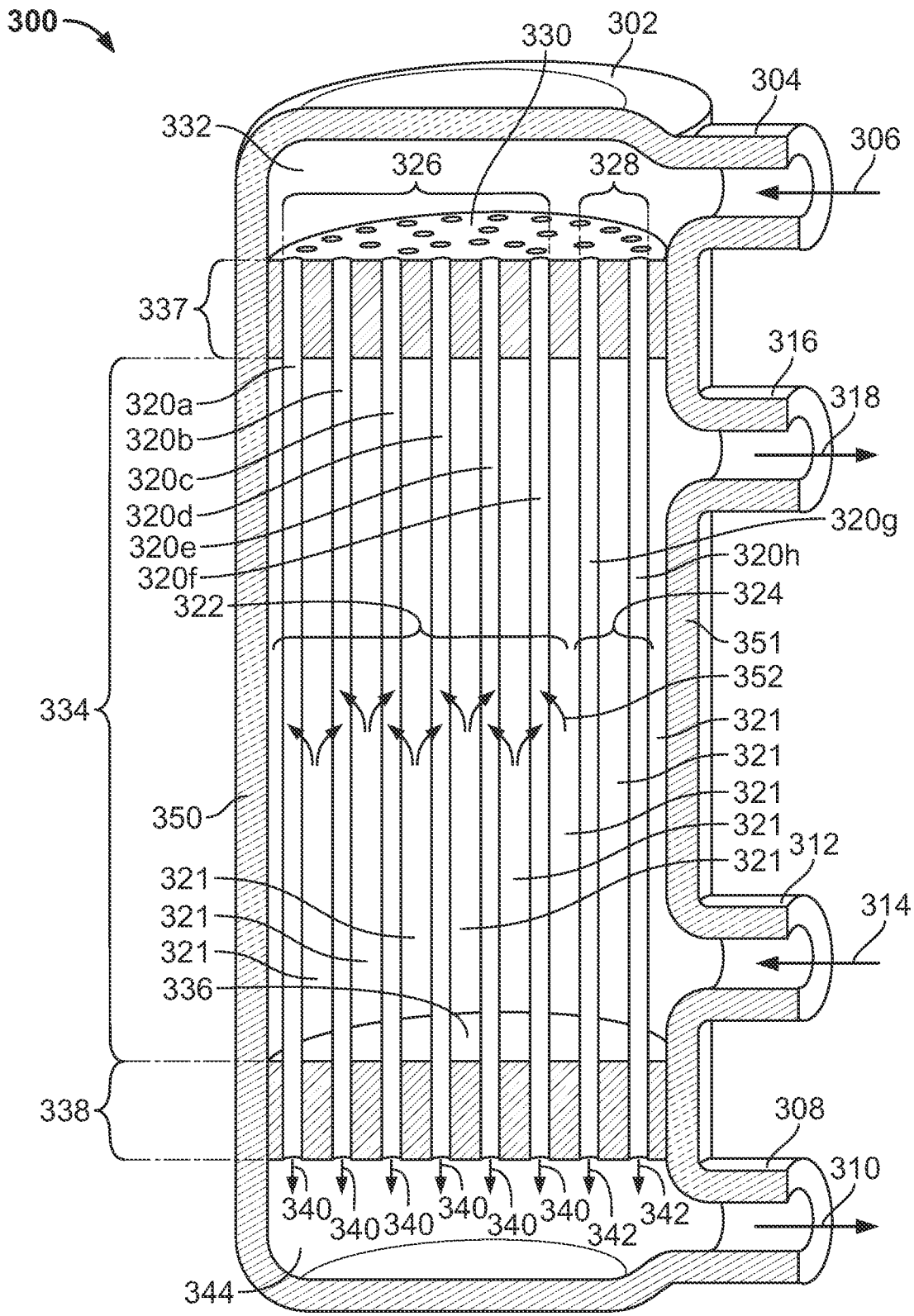
FIG. 2 shows an illustrative vapor transfer unit for humidity control.

FIG. 2 shows a vapor transfer unit 300 for humidity control, according to certain implementations. The vapor transfer unit 300 includes a housing 302 having a gas inlet 304, a gas outlet 308, a liquid inlet 312, and a liquid outlet 316. The housing 302 encloses a plurality of tubes 320a-h. The plurality of tubes 320a-h includes a first subset 322 of tubes 320a-f and a second subset 324 of tubes 320g-h. The tubes 320a-f of the first subset 322 are porous, while the tubes 320g-h of the second subset 324 are non-porous. The tubes 320a-h are supported at their ends 337 and 338 by plugs 330 and 336, respectively. The plugs 330 and 336 are disk-shaped and are held in place by the walls 350 and 351 of the housing 302. The plugs 330 and 336 also define the upper and lower boundaries of the liquid region 321 to enclose the liquid region 321. Thus, the plugs 330 and 336 separate the liquid region 321 from the upper chamber 332 and lower chamber 344, through which gas passes. The liquid region 321 is in fluid communication with the liquid inlet 314 and the liquid outlet 318.

In use, gas 306 passes through the gas inlet 304 into a top chamber 332. The gas then passes into the plurality of tubes 320a-h, through tube inlets 326 and 328. The gas that enters the tube inlets 326 passes through the first subset 322 of porous tubes 320a-f and is humidified in the humidification region 334. The number of tubes in the first subset 322 is sufficient to allow the gas passing therethrough to be humidified to nearly 100% relative humidity. Increasing the number of porous tubes 320a-f causes the humidified gas fraction 340 to have a higher relative humidity (e.g., closer to 100%), while decreasing the number of porous tubes 320a-f causes the humidified gas fraction 340 to have a lower relative humidity. As the gas flows into the humidification region 334, heated liquid 314 enters the liquid inlet 314 and passes through the liquid region 321. In the liquid region 321, the liquid passes over the outer surfaces of the tubes 320a-h. Vapor is transferred from the liquid in region 321 to the gas passing through the porous tubes 320a-f in the humidification region 334 as indicated by arrows 352. Although the arrows 352 only show the transfer of vapor at one location along the length of tubes 320a-f, the vapor transfer occurs along the length of tubes 320a-f in the humidification region 334. After passing through the liquid region 321, the liquid 318 exits the liquid outlet 316. The gas that enters the tube inlets 328 passes through the second subset 324 of non-porous tubes 320g-h. Since the second subset 324 of tubes 320g-h are nonporous, vapor cannot transfer from the liquid region 321 to the gas flowing through the second subset 324 of tubes 320g-h. This prevents the gas flowing through the second subset 324 of tubes 320g-h from being humidified. The second subset 324 of non-porous tubes 320g-h may be extruded plastic tubes. In some implementations, the second subset 324 of tubes 320g-h are porous, but liquid is not supplied to the outer surfaces of the tubes 320g-h to prevent humidification of the gas flowing therethrough. Although no vapor is transferred through the second subset 324 of tubes 320g-h, The bypassed gas fraction 342 is still heated by the liquid circulating in the liquid region 321. The humidified gas fraction 340 and the bypassed gas fraction 342 exit the bottom region 338 of the first subset 322 and the second subset 324, respectively, of tubes 320a-h and mix in the bottom chamber 344. This forms a mixed output gas 310 having a relative humidity that does not change substantially with a change in gas flow rate and that is approximately equal to the percentage of tubes that are porous. For example, when about 80% of the tubes 320a-h are porous, the relative humidity of the mixed output gas may be about 80%.

The mixed output gas 310 exits the vapor transfer unit 300 through gas outlet 308. By allowing the bypassed gas 342 to mix with the humidified gas 344, the humidity level of the output gas 310 can be reduced to prevent humidity in the output gas 310 from condensing in the downstream flow path (not shown) when the output gas 310 cools. However, unlike the bypass passage 109 discussed in relation to FIGS. 1A and 1B, the fraction of bypassed gas 342 remains about constant as the flow rate changes. This is because as the gas flow rate through the gas inlet 306 increases, the flow resistance caused by the first subset 326 of porous tubes 320a-f increases at the same rate as the flow resistance caused by the second subset 324 of non-porous tubes 320g-h. Thus, the ratio of humidified gas 340 to bypassed gas 342 remains about constant as gas flow rates through the gas inlet 304 vary.

At high flow rates through the gas inlet 304, the gas flowing through the first subset 322 of permeable tubes 320a-f passes more quickly through the humidification zone 334 and has less time to receive vapor from liquid in the liquid region 321. Thus, at high flow rates, the relative humidity of the output gas 310 may fall if a sufficient quantity of tubes is not present. The increase in number of tubes increases the size and cost of the VTC. Therefore, it may be preferable to have a valve for selectively obstructing the non-porous tubes 320a-f at high flow rates to reduce the bypassed gas fraction 340 and prevent the output gas 310 from being excessively dry.

Figure 4:
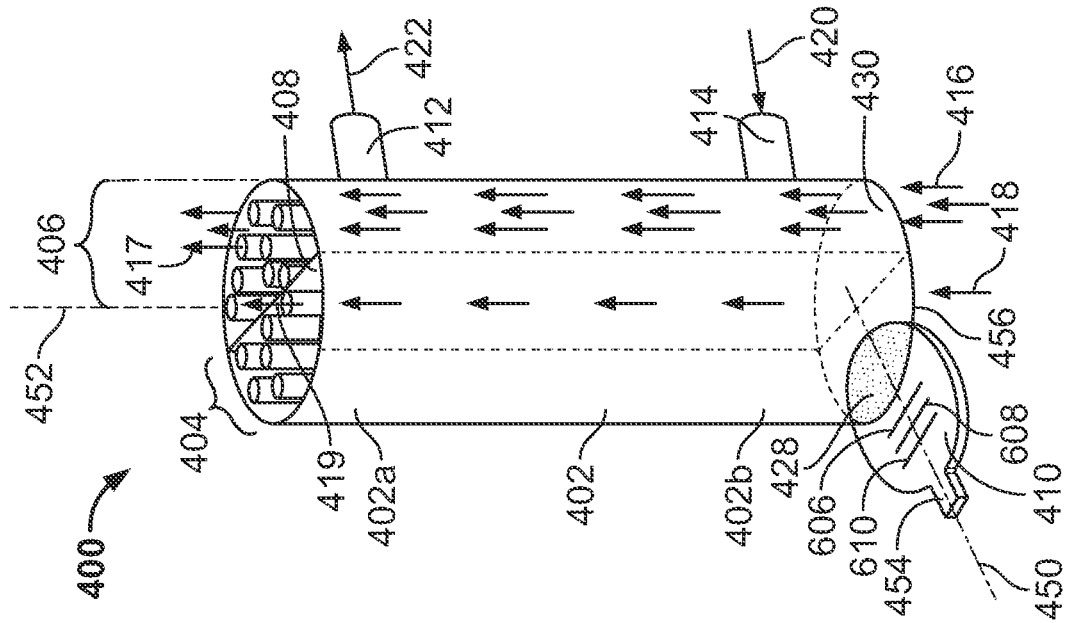
FIGS. 3 and 4 show a vapor transfer unit having a valve for selectively obstructing tubes.
Figure 3:
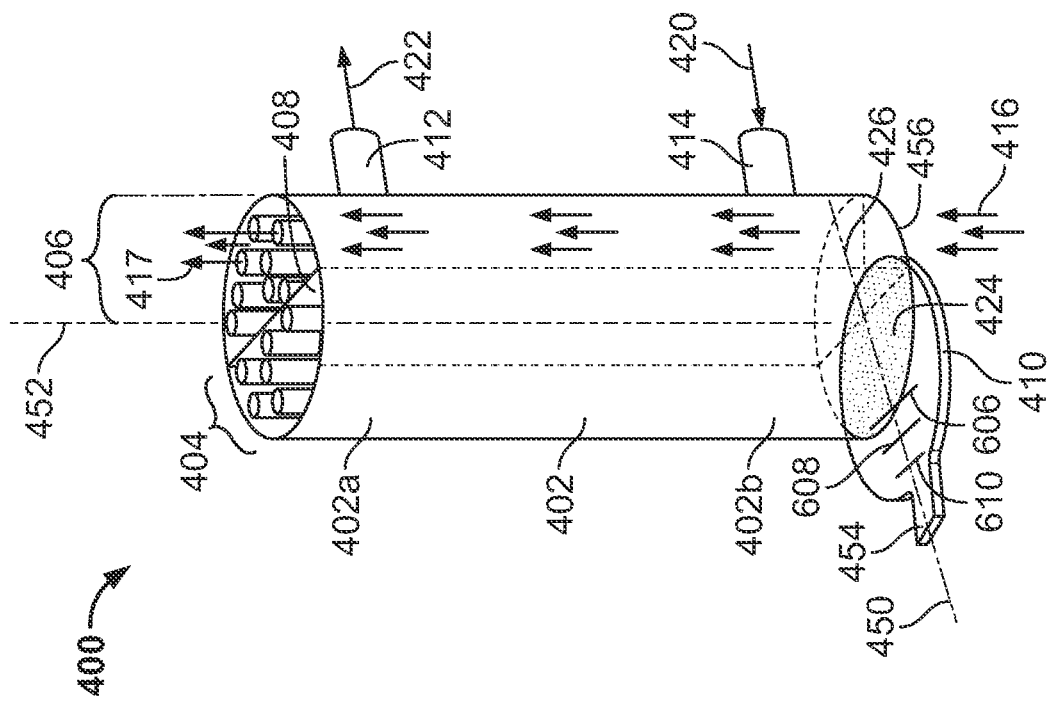

FIGS. 3 and 4 show a vapor transfer unit 400 having such a valve 410 for selectively obstructing tubes 404 and 406, according to certain implementations. The vapor transfer unit 400 is similar to the vapor transfer unit 300 in FIG. 2 and includes a housing 402, a first subset of tubes 404, and a second subset of tubes 406. The first subset of tubes 404 and the second subset of tubes 406 are functionally similar to the first subset 322 of tubes 320a-f and the second subset 324 of tubes 320g-h. The first subset of tubes 404 and the second subset of tubes 406 are separated by a divider 408. Liquid flows into inlet 414 and along outer surfaces of the tubes 404 and 406 before exiting from the liquid outlet 412. The housing 402 has an upper end portion 402a and a lower end portion 402b. The valve 410 is positioned against the lower end portion 402b of the housing 402. The valve 410 may be held against the lower end portion 402b by a fastener (not shown). The valve 410 is allowed to slide along an axis 450 perpendicular to the longitudinal axis 452 of the housing 402, while the valve 410 remains perpendicular to the longitudinal axis 452 of the housing 402. The valve 410 obstructs a cross section 424 of the lower end portion 402b housing 402 and leaves exposed a cross section 426 of the lower end portion of the housing 402. The valve 410 includes calibrated notches 610, 608 and 606, which allow a user to select a desired relative humidity of the output gas by aligning one of the notches 610, 608 or 606 with a bottom rim 456 of the housing 400. The valve 410 also includes a tab 454 which the user may push towards the housing 402 or pull away from the housing to increase or decrease, respectively, the cross section 424 that is obstructed. As a result, the valve 410 allows gas 416 to flow through the tubes 406, but obstructs gas flow through the tubes 404. The tubes 406 are porous, so the liquid 420 flowing through the housing 402 transfers vapor to the gas 416 through pores (not shown) in the tubes 406 as the liquid 420 flows from the lower end portion 402b to the upper end portion 402a of the housing 402. Thus, the liquid 420 humidifies the gas 416 that passes through the tubes 406, and the gas 416 exits the tubes 406 as humidified gas 417. The incoming gas 416 is supplied by a gas inlet, and the humidified gas 417 exits through a gas outlet, but these gas ports are omitted from FIGS. 3 and 4 for the sake of clarity.

In FIG. 4, the valve 410 is set so that it allows the gas 416 to pass through the tubes 416 and to allow gas 418 to pass through the tubes 404. The valve 410 is set by manually sliding the valve 410 along the axis 450 to set the cross section 428 of the lower end portion 402b of the housing 402 that is obstructed by the valve 410. Relative to the configuration shown in FIG. 3, the valve 410 in FIG. 4 has been displaced towards the housing 402 along the axis 450. This displacement can be achieved by a pressing the tab 454 towards the housing 402. In a preferred implementation, the displacement is provided manually, but the valve is 410 can also be displaced automatically by an electronic control system. As discussed above, the gas 416 is humidified as it passes through tubes 406 and exits the upper end portion 402a of the housing 402 as humidified gas 417. In contrast, the tubes 404 are non-porous, so the gas 418 is not humidified as it flows through the tubes 404 and exits the upper end portion 402a of the housing 402 as bypassed gas 419. In some implementations, the tubes 404 are porous, but liquid is prevented from contacting the tubes 404 to prevent humidification of the gas 418 as it passes through the tubes 404. For example, the tubes 404 can be covered with a potting compound to prevent liquid from contacting the tubes 404.

The humidified gas 417 and the bypassed gas 419 combine to form an output gas (not shown), which is similar to output gas 310 in FIG. 2. The relative humidity of the output gas is between the relative humidity of the humidified gas 417 and the relative humidity of the bypassed gas 419. The relative humidity of the output gas depends on the position of the valve 410. If the valve 410 is set so that it obstructs flow through all of the tubes 404, no bypassed gas 419 will mix with the humidified gas 417. As a result, the relative humidity of the output gas would be about equal to the relative humidity of the humidified gas 417. In some implementations the relative humidity of the humidified gas 417 is high (e.g., >70%, >80%, >90%, >95%, >99%, or nearly 100%). If the valve 410 is set so that it allows flow through more of the tubes 404, a greater fraction of bypassed gas 419 is included in the output gas and the relative humidity level of the output gas drops. Therefore, the tubes 404 act as a bypass passage, similar to the bypass passage 109 of the vapor transfer unit 100. By allowing the tubes 404 to be open at low flow rates and obstructed by the valve 410 at high flow rates, condensation can be reduced at low flow rates, while maintaining high humidity and preventing a significant drop in humidity at high flow rates. A significant drop in humidity may be a reduction in the relative humidity of >40%, >30%, >20%, >15%, >10%, >5%, or a similar reduction in relative humidity.

In certain implementations, the tubes 404 are porous like the tubes 406. In such implementations, the gas 419 is humidified when passing through tubes 404 similar to how gas 417 is humidified when passing through tubes 406. The humidity level of the output gas is controlled by varying the total number of tubes 404 and 406 that are obstructed by the valve 410. Increasing the total number of tubes 404 and 406 obstructed by the valve 410 decreases the total number of tubes 404 and 406 exposed to the flow of gas 416 and 418. This decreases the surface area available for the transfer of vapor to the gas and thus decreases the relative humidity of the output gas. In some of these implementations, both the tubes 404 and 406 are exposed to gas flow when the gas flow rates are above a threshold, and the tubes 404 are obstructed by the valve 410 at rates below the threshold. The threshold may be about 8 L/min, 20 L/min, 30 L/min, 40 L/min or any other suitable flow rate. The change in the number of tubes 404 and 406 exposed to gas flow can be done by sliding the valve 410 along the axis 450. The sliding of the valve 410 can be done manually by a user or automatically by an electronic control system. In some implementations, when the valve 410 is set so that all the tubes 404 and 406 are exposed to the flow of gas 416 and 418, the effective area for humidification is about 100 square centimeters, and when the valve 410 is set so that tubes 404 are obstructed by valve 410, the effective area for humidification is about 50 square centimeters. Since the humidity of the output gas tends to drop as the rate of flow of gas 416 and 418 through the housing 402 increases, allowing more tubes to be exposed to the flow of gas 416 and 418 at higher flow rates can counteract this drop in humidity. In contrast, the relative humidity of the output gas tends to rise as the rate of gas flow through the housing 402 decreases. Therefore, reducing the number of tubes 404 and 406 exposed to the gas flow using the valve 410 can reduce the humidity of the output gas which can prevent excess humidity from causing condensation. Thus a single vapor transfer unit 400 can be used to provide adequate humidity at both low and high flow rates using the valve 410.

Although the humidity of the output gas of the vapor transfer unit 400 is controlled by controlling the flow of gas 416 and 418 through the tubes 404 and 406, in some implementations, the humidity of the output gas is controlled by changing the number of tubes 404 and 406 exposed to the flow of liquid 420. For example, in some implementations, the number of tubes 404 and 406 that are exposed to the flow of the liquid 420 can be altered using a valve (not shown). The valve allows the user to select whether the liquid 420 entering the liquid inlet 414 is admitted on both sides of the divider 408. The divider 408 allows the flow of the liquid 420 around the tubes 406 to be isolated from the flow of the liquid 420 around the tubes 404. The number and type of exposed tubes can be varied by use of the valve. In a first position, the valve can allow the liquid 420 to flow around the tubes 406. In a second position, the valve can allow liquid 420 to flow around the tubes 406 and 408. When only the tubes 406 are exposed to the flow of liquid 420 and both the tubes 404 and 406 are exposed to gas flow, only half of the output gas is humidified. When the tubes 404 and 406 are both exposed to the flow of liquid 420, all of the output gas is humidified. Thus, by changing the number of tubes 404 and 406 exposed to the flow of the liquid 420, the humidity of the output gas can be controlled.

Figure 5:
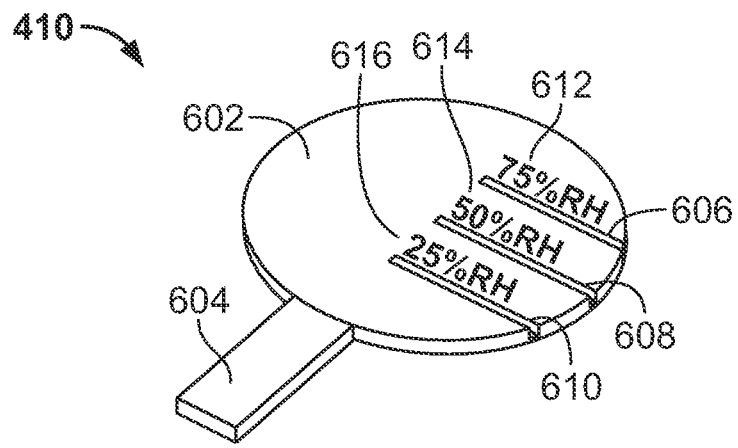
FIG. 5 shows an illustrative valve for selectively obstructing the tubes of FIGS. 3 and 4.

FIG. 5 shows a perspective view of the valve 410 of the vapor transfer unit 400 of FIGS. 3 and 4. The valve 410 includes a valve body 602 and a tab 604. The valve body includes notches 606, 608, and 610 and corresponding labels 612, 614, and 616, respectively. The labels 612, 614, and 616, indicate the relative humidity of the output gas of the vapor transfer unit 400 that is achieved when the valve 410 is set such that the notches 606, 608, or 610 are aligned with the bottom rim 456 of the housing 402 of vapor transfer unit 400. Aligning the notches 606, 608, and 610 with the bottom rim 456 of the housing 402 leaves open a cross section of the lower end portion 402b of the housing 402, such as cross section 430 in FIG. 4.

In use, the tab 604 is manipulated by a user to adjust the area of the valve body 602 that is used to obstruct gas flow. A user may select a desired humidity level and move the valve 410 to the position corresponding thereto using the labels 612, 614, and 616. For example, to select a desired relative humidity of 75%, the notch 606 would be aligned with the bottom rim 456 of the vapor transfer unit 400 as shown in of FIG. 4, leaving exposed a cross section 430 of the lower end portion 402b of the housing 402. The area 428 obstructed by the valve 410 is increased (to decrease the humidity) by pressing the tab 604 until the notch with the desired humidity level aligns with the bottom rime 456 of the housing 402. The area 428 obstructed by the valve 410 can similarly be decreased (to increase the humidity) by pulling the tab 604 to displace the valve 410 away from the housing 402. As the area obstructing gas flow decreases, more bypassed gas is mixed into the gas output, and the humidity level of the gas output drops. Thus, by positioning the notches 606, 608, and 610, the valve 410 allows precise manual control of the humidity levels of the output gas. Although the notches 606, 608, and 610 indicate relative humidity levels of 75%, 50%, and 25%, the valve may be marked with any suitable number of notches to indicate any suitable relative humidity level, including relative humidity levels over 75%. For example, the relative humidity levels indicated on the valve 410 can include 80%, 90%, 95%, 99%, and nearly 100%. In some implementations, the valve 410 may be automatically controlled. For example, the valve 410 can be actuated by an electromechanical control system. The electromechanical control system can use a humidity sensor to monitor the humidity of the output gas and adjust the valve 410 accordingly.

Figure 6:
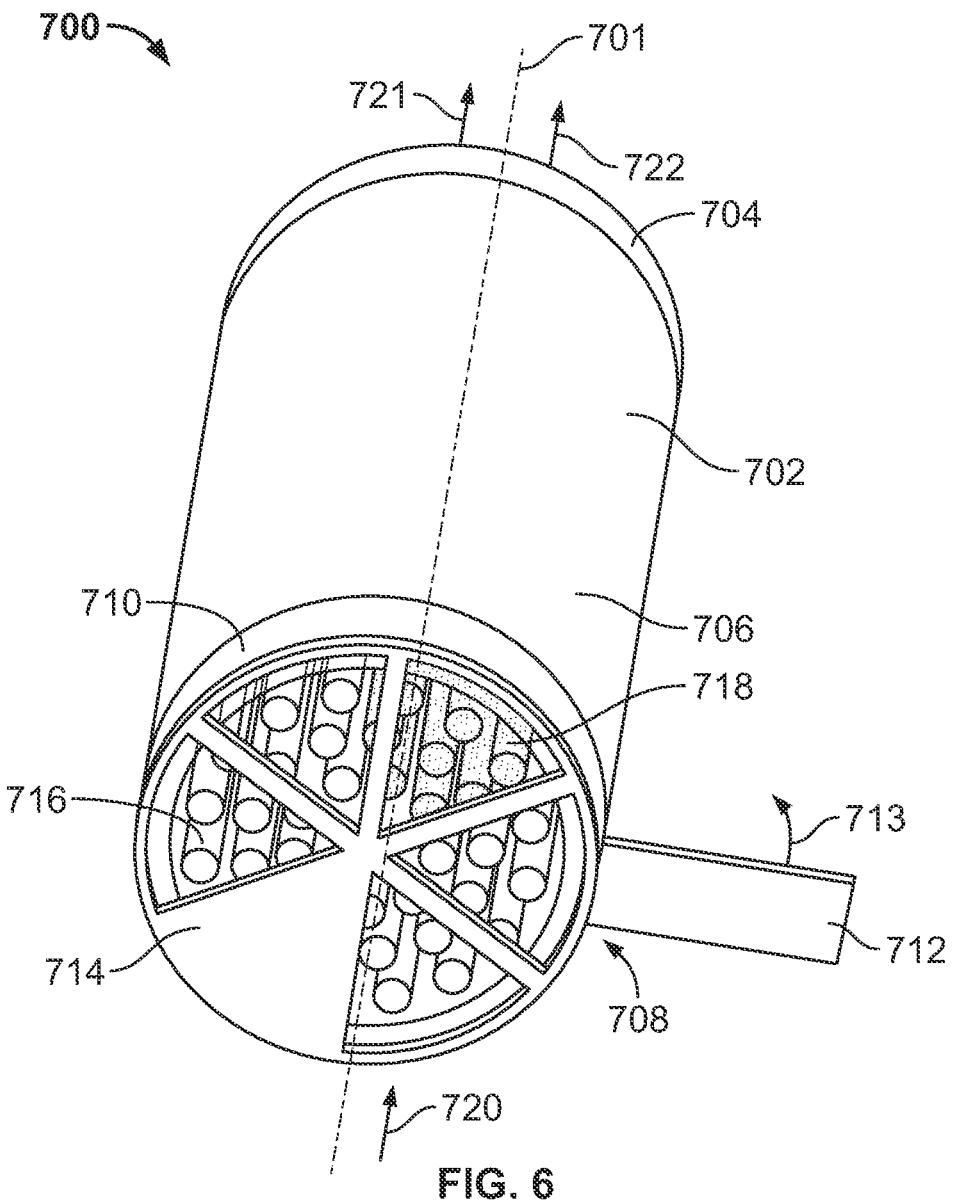
FIG. 6 shows a vapor transfer unit having a rotating valve for selectively obstructing tubes.

While the valve 410 of vapor transfer unit 400 is a sliding valve, other valve configurations can be used. FIG. 6 shows a vapor transfer unit 700 having a rotating valve 708 for selectively obstructing tubes 716 and 718, according to certain implementations. The vapor transfer unit 700 includes the rotating valve 708 and a housing 702 having a longitudinal axis 701, a first end portion 704, and a second end portion 706 opposite the first end portion 704. Disposed within the housing 702 are a first group of porous tubes 716 and a second group of non-porous tubes 718, each tube extending longitudinally within the housing 702 along the longitudinal axis 701. In some implementations, the tubes 718 are porous, but liquid is prevented from contacting the tubes 718 to prevent humidification of gas passing therethrough. The rotating valve 708 includes a tab 712, a rim 710, and a cover 714. The cover 714 prevents gas flow 720 from passing through the subset of tubes behind the cover 714 (not shown). The rim 710 of the rotating valve 708 is coupled to the second end portion 706 of the housing 702. The coupling between the rotating valve 708 and the second end portion 706 of the housing 702 allows the rotating valve 708 to rotate relative to the housing 702 about the longitudinal axis 722, as indicated by the arrow 713. The tab 712 is used to rotate the rotating valve 708 and thereby change the subset of tubes obstructed by the cover 714. The tab 712 can be rotated manually or automatically by an electronic control system.

In use, gas 720 flows through the vapor transfer unit 700 from the second end portion 706 towards the first end portion 704 along the longitudinal axis 722. The gas 720 flows through the interior of the tubes 716 and 718 that are not obstructed by the cover 714. The gas that flows through the porous tubes 716 exits the vapor transfer unit 700 as humidified gas 721, while the gas that flows through the non-porous tubes exits the vapor transfer unit as bypassed gas 722. Rotating the rotating valve 708 about the longitudinal axis 701 changes the subset of tubes that are obstructed (not shown) and can change the ratio of unobstructed porous tubes 716 to unobstructed non-porous tubes 718. The ratio of unobstructed porous tubes 716 to unobstructed non-porous tubes 718 determines the amount of bypassed gas 722 that is mixed with humidified gas 721 to form the output gas (not shown). Thus, by rotating the valve 708, the relative humidity of the output gas can be controlled.

Figure 7:
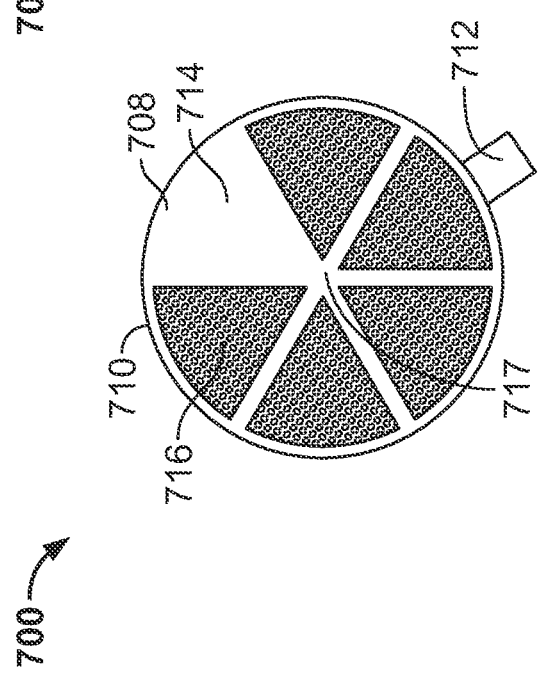
FIGS. 7-11 show bottom views of the vapor transfer unit of FIG. 6 having the rotating valve at various orientations.
Figure 8:
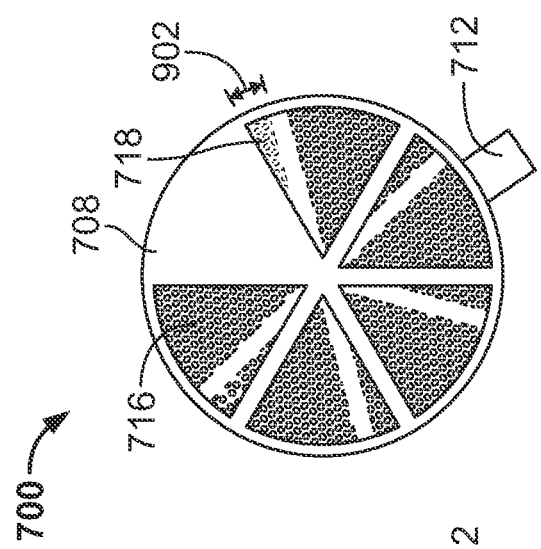
Figure 9:
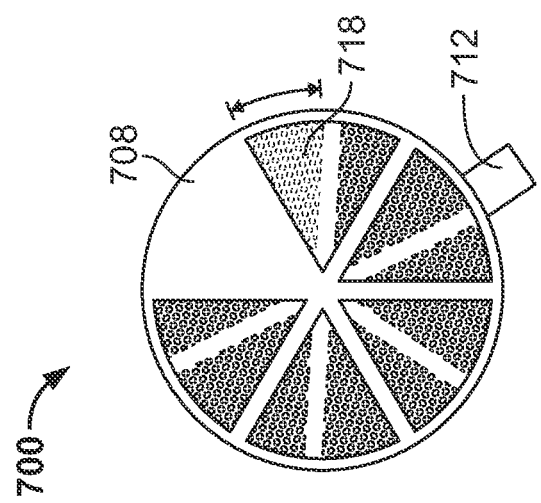
Figure 10:
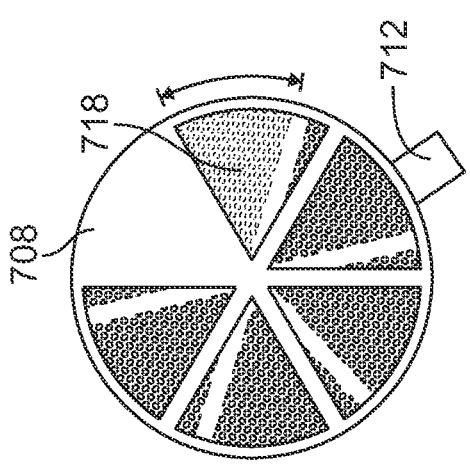
Figure 11:
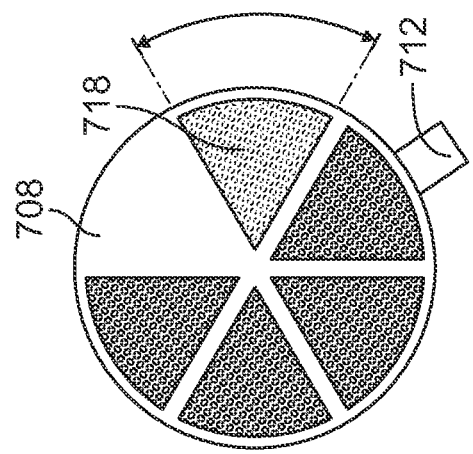

FIGS. 7-11 show bottom views of the vapor transfer unit 700 of FIG. 6 having the rotating valve 708 positioned in various orientations. In FIG. 7, the rotating valve is positioned so that the cover 714 completely obstructs flow through the non-porous tubes 718 (not shown). As a result, all the gas passing through the vapor transfer unit 700 would be humidified. Thus the output gas can have a relative humidity of about 100%. In FIG. 8, the valve 708 has been rotated by an angle 902 relative to the position in FIG. 7. As a result, gas flow is allowed through some of the non-porous tubes 718. Thus, a fraction of the gas passing through the vapor transfer unit 700 is not humidified and exits as bypassed gas. In FIG. 8, the ratio of unobstructed porous tubes 716 to unobstructed non-porous tubes 718 is about 19. In other words, about 95% of the gas passing through the vapor transfer unit 700 is humidified while 5% is bypassed. The mixture of the small percentage of bypassed gas slightly lowers the relative humidity of the gas output in FIG. 8 relative to FIG. 7. In FIG. 9, the valve 708 has been rotated relative to FIG. 8 to expose more non-porous tubes 718. The ratio of unobstructed porous tubes 716 to unobstructed non-porous tubes 718 is about 9. Therefore, about 90% of the gas passing through the vapor transfer unit 700 is humidified while 10% is passed as bypassed gas. The mixture of more bypassed gas in FIG. 9 relative to FIG. 8 reduces the relative humidity of the output gas in FIG. 9 relative to FIG. 8. In FIG. 10, the valve has been rotated even further than in FIG. 9. As a result, the ratio of unobstructed porous tubes 716 to unobstructed non-porous tubes 718 is lower still, about 5.7. The output gas in FIG. 10 is about 85% humidified gas and 15% bypassed gas. Finally, FIG. 11 shows the valve 708 in the position in which the gas output has the lowest humidity possible with the particular valve configuration depicted. In FIG. 11, the ratio of unobstructed porous tubes 716 to unobstructed non-porous tubes 718 is 5 and the output gas is about 80% humidified gas and 20% bypassed gas. Thus, FIGS. 7-11 show that, various output relative humidity levels can be achieved by rotating the valve 708 relative to the vapor transfer unit 700.

FIGS. 12-16 show bottom views of a vapor transfer unit 1300 having a rotating valve 708, according to certain implementations. The vapor transfer unit 1300 includes porous tubes 1316. Unlike the vapor transfer unit 700 depicted in FIGS. 6-11, the vapor transfer unit 1300 does not include non-porous tubes. Instead, the vapor transfer unit 1300 includes a blocked section 1318 which does not admit the flow of gas. In FIG. 12, the valve 708 is positioned to allow gas flow through all or nearly all of the tubes 1316. Therefore, the position of the valve 708 in FIG. 12 corresponds to the maximum humidification possible using the vapor transfer unit 1300 having the particular design depicted in FIGS. 12-16. In some implementations, when the valve 708 is in the position depicted in FIG. 12, the effective area available for vapor transfer is 100 square centimeters.

In FIG. 13, the valve 708 has been rotated to expose some of the blocked section 1308 and to obstruct a portion of the porous tubes 1316. As a result, the total number of tubes 1316 exposed to the flow of gas through the vapor transfer unit 1300 is reduced in FIG. 13 relative to FIG. 12. In FIG. 13, about 95% of the tubes 1316 disposed within the vapor transfer unit 1300 are exposed to gas flow. In FIG. 14, the valve 708 is positioned so that 90% of the tubes 1316 are exposed to the flow of gas. In FIG. 15, the valve 708 is positioned so that 85% of the tubes 1316 are exposed to the flow of gas. Finally, 80% of the tubes 1316 are exposed to the flow of gas in FIG. 16. Thus, by rotating the valve 708, varying amounts of porous tubes 1316 can be exposed to the flow of gas. At low flow rates, gas passes more slowly through the tubes 1316 and has more time for humidification to occur. If the flow rates are below a certain rate (e.g., 30 L/min, 20 L/min, 8 L/min, or another similar flow rate), the output gas may become excessively humid and cause condensation downstream in the circuit when the output gas cools slightly. To counteract this effect, the valve 708 can be rotated to reduce the number of tubes 1316 exposed to the flow of gas. As a result, the output gas can be prevented from reaching excessive levels of humidity.

At high flow rates, the gas passes through the porous tubes 1316 more rapidly, allowing less time for humidification. As a result, the output gas may have lower humidity levels at higher flow rates (e.g., >8 L/min, >20 L/min, >30 L/min, or another similar flow rate). Delivering breathing gas having inadequate humidity (e.g., humidity of <99%, <95%, <90%, <80%, or at some similar humidity level) can cause patient discomfort at high flow rates due to drying of a patient's respiratory tract. To prevent the humidification at high flow rates from being reduced, the valve 708 can be positioned to allow gas flow through a high percentage of or all of the porous tubes 1316. Thus by adjusting the total number of tubes 1316 exposed to gas flow, the humidity of the output gas can be controlled to prevent condensation at low flow rates and to prevent inadequate humidification at high flow rates.

FIG. 17 shows an exploded view of a vapor transfer unit 1900 having a rotatable housing 1908, according to certain implementations. The vapor transfer unit 1900 is similar to the vapor transfer unit 700 shown in FIG. 6. The vapor transfer unit 1900 includes a housing 1908 having a longitudinal axis 1950, an upper end 1908a, a lower end 1908b, a low flow label 1912, a high flow label 1914, and an end cap 1902. The end cap 1902 mates with the lower end 1908b of the housing 1908 such that the housing 1908 can rotate relative to the end cap 1902. Disposed within the housing 1908 are a plurality of tubes 1920 and 1930 that extend longitudinally along the longitudinal axis 1950 of the housing 1908. The tubes 1920 are non-porous and the tubes 1930 are porous. The non-porous tubes 1920 are scattered among the porous tubes 1930. In some implementations, the ratio of porous tubes to non-porous tubes is 1:4.

The end cap 1902 includes a cover 1904, for obstructing the portion of the tubes 1920 and 1930 located behind the cover 1904 and an opening 1906 for admitting gas flow 1903 through the remainder of the tubes 1920 and 1930. The end cap 1902 functions similarly to the valve 708 in FIG. 6, but the end cap 1902 remains stationary relative to the humidification system (not shown) while the housing 1908 and tubes 1920 and 1930 rotate. Since the non-porous tubes 1920 are scattered among the porous tubes 1930, rotating the housing 1908 and the tubes 1920 and 1930 relative to the end cap 1902 does not significantly change the ratio of porous tubes 1930 to non-porous tubes 1920 aligned with the opening 1906 of the end cap 1902.

In use, incoming gas 1901 flows through the tubes 1920 and 1930 that are aligned with the opening 1906 in the end cap 1902. Meanwhile, liquid (not shown) is circulated within the housing 1908 between the tubes 1920 and 1930. The liquid transfers vapor to the gas 1901 as it flows through the porous tubes 1920 that are aligned with the opening 1906 in the end cap 1902. Since the non-porous tubes 1920 are scattered among the porous tubes 1930, rotating the housing 1908 and the tubes 1920 and 1930 relative to the end cap 1902 does not significantly change the ratio of porous tubes 1930 to non-porous tubes 1920 exposed to the flow of incoming gas 1903. Thus, the amount of vapor transferred to the gas 1901 and the relative humidity of the output gas 1903 is not significantly affected by rotating the housing 1908 and tubes 1920 and 1930 relative to the end cap 1902.

When the housing 1908 is rotated relative to the end cap 1902, the labels 1912 and 1914 are also rotated. An optical sensor 1962 detects the label that is in its line of sight 1960. Thus, rotating the housing 1908 changes which label is exposed to the optical sensor 1962. The optical sensor configures the flow settings for the overall humidification system (not shown) based on the label that is detected. The optical sensor can be a camera, a bar code scanner, an infrared sensor, or any other suitable sensor. As shown in FIG. 17, the high flow label 1912 is aligned with the line of sight of 1960 of the optical sensor 1962. As a result, the optical sensor 1962 detects the presence of a high flow vapor transfer unit and configures the humidification system for operation at high flow rates. When a high flow vapor transfer unit is detected, the humidification system may be permitted to operate at higher flow rates than when a low flow vapor transfer unit is detected. When the labels 1912 and 1914 are rotated to align the low flow label 1914 with the line of sight 1960 of the optical sensor 1962, the optical sensor 1962 detects the presence of a low flow vapor transfer unit and configures the humidification system for operation at low flow rates. By controlling which label is exposed to the optical sensor 1962, the high flow therapy system can be enabled to use a single vapor transfer unit 1900 at either the high flow or low flow settings. This enables the vapor transfer unit 1900 to be retrofitted for use with existing high flow therapy systems that are configured to operate with separate vapor transfer units for high and low flow.

FIG. 18 shows an exploded view of a vapor transfer unit 2000 with a rotatable housing 2008, according to certain implementations. The vapor transfer unit 2000 is similar to the vapor transfer unit 1900 shown in FIG. 17 and the vapor transfer unit 700 shown in FIG. 6. The vapor transfer unit 2000 includes a housing 2008 having a longitudinal axis 2050, an upper end 2008a, a lower end 2008b, a low flow label 2012, a high flow label 2014, and an end cap 2002. The end cap 2002 mates with the lower end 2008b of the housing 2008 such that the housing 2008 can rotate relative to the end cap 2002. Disposed within the housing 2008 are a plurality of tubes 2020 and 2030 that extend longitudinally along the longitudinal axis 2050 of the housing 1908. The tubes 2030 are porous and the tubes 2020 are blocked to prevent gas flow. Unlike the scattered non-porous tubes 1920 in vapor transfer unit 1900, the blocked tubes 2020 are grouped together. In some implementations, the ratio of porous tubes to blocked tubes is 1:3.

The end cap 1902 includes a cover 1904, for obstructing the portion of the tubes 2030 located behind the cover 1904 and an opening 1906 for admitting gas flow 2003 through the remainder of the tubes 2030. (The tubes 2020 are blocked by design, so they do not require the end cap to block flow through them.) The end cap 1902 functions similarly to the end cap of FIG. 17. The end cap 1902 remains stationary relative to the humidification system (not shown) while the housing 2008 and tubes 2020 and 2030 rotate. The blocked tubes 2020 are grouped in the low flow side 2011 of the housing 2008 labeled with the high flow label 2012.

In use, incoming gas 2001 flows through the tubes 2030 that are aligned with the opening 1906 in the end cap 1902. Meanwhile, liquid (not shown) is circulated within the housing 1908 between the tubes 2020 and 2030. The liquid transfers vapor to the gas 2001 as it flows through the porous tubes 2020 that are aligned with the opening 1906 in the end cap 1902. Since the blocked tubes 2020 are grouped on the low flow side 2011 of the housing 2008, when the low flow side 2011 of the housing 2008 is aligned with the opening 1906 in the end cap 1902, fewer porous tubes 1920 are exposed to the gas flow 2001. In some implementations, the number of porous tubes 2030 exposed to the flow 2001 at high flow rates is twice the number of porous tubes exposed to the flow 2001 at low flow rates. The surface area available for vapor transfer may be 100 square centimeters at high flow rates and 50 square centimeters at low flow rates. While the tubes 2020 are blocked in vapor transfer unit 2000, in some implementations, the tubes 2020 are non-porous and admit air flow. Thus, the amount of vapor transferred to the gas 2001 and the relative humidity of the output gas 2003 is significantly lower when the low flow side 2011 of the housing is aligned with the opening 1906 in the end cap 1902.

When the housing 2008 and tubes 2020 and 2030 are rotated relative to the end cap 1902, the labels 2012 and 2014 are also rotated. An optical sensor 1962 detects the label that is in its line of sight 1960 and configures the flow settings for the overall humidification system (not shown) based on the label that is detected. The optical sensor can be a camera, a bar code scanner, an infrared sensor, or any other suitable sensor. As shown in FIG. 17, the high flow label 2012 is aligned with the line of sight of 1960 of the optical sensor 1962. As a result, the optical sensor 1962 detects the presence of a high flow vapor transfer unit and configures the humidification system for operation at high flow rates. Additionally, when the housing 2008 is so positioned, the tubes on the high flow side 2007 of the housing are exposed to the flow of gas 2001. When the high flow vapor transfer unit is detected, the humidification may be permitted to operate at higher flow rates than when a low flow vapor transfer unit is detected.

When the blocked tubes 2020 are aligned with the opening 1906 of the end cap 1902, the low flow label 2008 is positioned in the line of sight 1960 of the optical sensor. When this occurs, the optical sensor detects the presence of a low flow vapor transfer unit and configures the humidification system for operation at low flow rates. The configuration of the humidification system may include a setting for a maximum flow rate for flowing the gas 2001 through the vapor transfer unit 2020 to prevent inadequate humidification of the output gas 2003. The labels 2012 and 2014 allow the humidification system to adjust its settings based on whether the positioning of tubes 2020 and 2030 correspond to the high flow or low flow configurations. This enables the vapor transfer unit 2000 to be operated at both high and low flow rates. In some implementations, the optical sensor can detect intermediate positions between high and low flow rate configurations and can adjust the settings of the humidification system accordingly.

FIGS. 19A-19D show illustrative bypass units 2100 (FIG. 19A), 2120 (FIG. 19B), 2140 (FIG. 19C), and 2160 (FIG. 19D) having different output humidity levels. In FIG. 19A bypass unit 2100 includes a first vapor transfer unit 2102 and a second vapor transfer unit 2104. The first vapor transfer unit includes a gas inlet 2106, a gas outlet 2108, a liquid inlet 2114, and a liquid outlet 2116. The second vapor transfer unit includes a gas inlet 2110, a gas outlet 2112, a liquid inlet 2118, and a liquid outlet 2119. The gas inlet 2110 of the second vapor transfer unit is connected to an upstream end 2101 of the first vapor transfer unit 2102, and the gas outlet 2112 of the second vapor transfer unit 2104 is connected to a downstream end 2103 of the first vapor transfer unit 2102.

In use, the gas inlet 2106 of the first vapor transfer unit 2102 is coupled to a gas source and output gas exits the gas outlet 2108. Gas flowing into the gas inlet 2106 flows through both vapor transfer units 2102 and 2104 in parallel. At the same time, liquid is passed into the liquid inlet 2114 and out of the liquid outlet 2116 of the vapor transfer unit 2102, but no liquid is passed through the liquid inlet 2118 of the second vapor transfer unit 2104. As a result, the gas flowing through the first vapor transfer device 2102 is humidified while the gas passing through the second vapor transfer device 2104 is not humidified. The humidified gas from the first vapor transfer unit 2102 and the bypassed gas from the second vapor transfer unit 2104 mix in the downstream end 2103 of the first vapor transfer unit 2102 to form the output gas. The ratio of gas passed through the first vapor transfer unit 2102 to the gas passed through the second vapor transfer unit 2104 determines the relative humidity of the output gas. The vapor transfer unit 2102 has the same number of tubes (not shown) disposed within its housing and the same internal flow resistance as does the vapor transfer unit 2104. Therefore, the amount of gas flow through the first vapor transfer unit 2102 is about equal to the amount of gas flow through the second vapor transfer unit 2104. As a result, 50% of the gas flow passing through the bypass unit 2100 is humidified, while 50% of the gas flow is not humidified. Thus, if the gas passed through the first vapor transfer unit 2012 has a relative humidity of about 100% and the gas passed through the second vapor transfer unit has a relative humidity of about 0%, then the relative humidity of the output gas is about 50%.

The bypass units 2120 in FIG. 19B and 2140 in FIG. 19C have configurations similar to the bypass unit 2100, but each bypass unit 2120 and 2140 includes a different combination of vapor transfer units. In FIG. 19B, bypass unit 2120 includes a high flow vapor transfer unit 2122 and a low flow vapor transfer unit 2124. The low flow vapor transfer unit 2124 has half the number of tubes (not shown) disposed within its housing as does the high flow vapor transfer unit 2122. Therefore, the low flow vapor transfer unit 2124 has about twice the flow resistance of the high flow vapor transfer unit 2122. Thus, the bypass unit 2120 causes two thirds (about 67%) of its gas input to be humidified and one third (about 33%) of its gas input to bypass humidification. As a result, the relative humidity of the output gas produced by bypass unit 2140 can be about 67%. In FIG. 19C, bypass unit 2140 includes a high flow vapor transfer unit 2142 and a low flow vapor transfer unit 2144. The low flow vapor transfer unit 2144 has a quarter the number of tubes (not shown) disposed within its housing as does the high flow vapor transfer unit 2142. As a result, the low flow vapor transfer unit 2144 has about four times the flow resistance of the high flow vapor transfer unit 2142. As a result, 80% of the gas flow into bypass unit 2140 is humidified, while 20% of the gas flow bypasses humidification. Thus, by connecting pairs of individual vapor transfer units, bypass units 2100, 2120, and 2140 can achieve various relative humidity output levels below 100%.

FIG. 19D shows a bypass unit 2160, including a single vapor transfer unit 2162 and a bypass tube 2164. The vapor transfer unit 2162 includes a gas inlet 2166, a gas outlet 2168, a liquid inlet 2174, and a liquid outlet 2176. A first fraction (not shown) of the gas entering the gas inlet 2166 is passed through the vapor transfer unit 2162 and is humidified by liquid that enters the liquid inlet 2174. A second fraction (not shown) of the gas entering the gas inlet 2166 is passed through the bypass tube 2164 and bypasses humidification. The humidified gas mixes with the bypassed gas in the downstream end 2163 of the vapor transfer unit 2160 and exits the gas outlet 2168 as output gas. The bypass tube 2164 includes a small orifice (not shown) having a diameter of 0.040 in (about 1 mm). The orifice causes the fraction of the gas flow passed through the bypass tube 2164 to decrease as the flow rate increases. As a result, a greater fraction of gas is passed through the bypass tube 2164 at low flow rates and a smaller fraction of gas is passed through the bypass tube 2164 at low flow rates. This change in the fraction of bypassed gas in response to flow rate helps to prevent excessive humidification at low flow rates to prevent or reduce condensation, while not significantly decreasing humidity at high flow rates.

The bypass units 2100, 2120, 2140, and 2160 were constructed and tested by Applicant. A prior art vapor transfer unit (a High Flow Vapor Transfer Cartridge supplied by Vapotherm, Inc., Exeter, NH), was also tested for comparison. The results of the tests are shown in FIG. 20. To construct the bypass units 2100, 2120, and 2140, pairs of vapor transfer units were connected to allow flow communication between the two gas inlet ports and between the two gas outlet ports of the connected vapor transfer units. Only one of the two vapor transfer units was supplied with a flow of water while the other vapor transfer unit had its liquid inlet and liquid outlet sealed.

Table 1 indicates the configurations of bypass units 2100, 2120, and 2140 in FIGS. 19A-19C. The first column indicates the bypass unit by reference numeral. The second column indicates the percentage of gas that is humidified and the percentage of gas that bypasses humidification. The humidification vapor transfer unit column identifies the vapor transfer unit that was connected to a water source for humidification. The bypassing vapor transfer unit column indicates the type of vapor transfer unit that was used to bypass the humidification vapor transfer unit. The high flow vapor transfer units had twice the number of tubes as the low flow vapor transfer units. Additionally, the low flow vapor transfer unit 2144 used to fabricate the bypass unit 2140 in FIG. 19C had 50% of its tubes blocked. Therefore, the low flow vapor transfer unit 2144 used in the bypass unit 2140 had a quarter the number of available tubes that the high flow vapor transfer units 2102, 2122, and 2142 had. By connecting the different pairs of individual vapor transfer units to fabricate the bypass units 2100, 2120, and 2140, different ratios of percent humidified gas to percent bypassed gas were achieved.

TABLE 1

Percent of Humidified Gas for Bypass Units

| Bypass Unit | Humidified %/ Bypass % | Humidification Vapor Transfer Unit | Bypassing Vapor Transfer Unit |
| --- | --- | --- | --- |
| 2100 | 50%/50% | High Flow | High Flow |
| 2120 | 67%/33% | High Flow | Low Flow |
| 2140 | 80%/20% | High Flow | Low Flow with 50% blocked |

The bypass unit 2160 in FIG. 19D was fabricated using a high flow rate vapor transfer unit 2162 and a bypass tube 2164 having a 0.25 in (6.35 mm) outer diameter. The tube was bonded to the outside of the vapor transfer unit 2162. The orifice (not shown) was formed by drilling a 0.040 in (1.02 mm) diameter hole into the vapor transfer unit 2162 at the point where the vapor transfer unit 2162 connects to the bypass tube 2160.

The humidity data plotted in FIG. 20 was gathered using capacitive humidity sensors (Sensirion). For each bypass unit and for the prior art vapor transfer unit, humidity was measured at a distal end of a delivery tube that was connected to the available gas outlet. The gas flow rate was initially set to 40 L/min, and the vapor transfer units were allowed to reach steady state. After a steady state was achieved, data logging was initiated, and the flow rate was reduced by 1 L/min increments every 30 seconds.

FIG. 20 shows a plot of relative humidity as a function of gas flow rate for the bypass units 2100, 2120, 2140, and 2160 of FIGS. 19A-19D and for a prior art vapor transfer unit. The x-axis 2202 of the plot represents the total gas flow rate measured in L/min. The y-axis 2204 represents the percent relative humidity of the output gas. The humidity curves 2206, 2208, 2210, 2212, and 2214 correspond to a prior art vapor transfer unit, bypass unit 2160 in FIG. 19D, bypass unit 2140 in FIG. 19C, bypass unit 2120 in FIG. 19B, and bypass unit 2100 in FIG. 19A, respectively. The humidity curve 2206 of the prior art vapor transfer unit shows that the relative humidity is significantly above 90% for flow rates below 30 L/min, and drops relatively steeply for flow rates in the range of 30-40 L/min. The high relative humidity of the prior art vapor transfer unit at the low flow rates causes condensation to occur when the output gas cools slightly. The humidity curves 2210, 2212, and 2214 demonstrate more consistent humidity levels than the prior art system. At low flow rates, the humidity curves 2210, 2212, and 2214 each exhibit a relative humidity about equal to the percent of the gas that passes through the humidification vapor transfer unit of the corresponding bypass unit. For example, the humidity curve 2214 initially shows a relative humidity of about 50%, and the bypass unit 2100 in FIG. 19A, to which the curve corresponds, passes 50% of its gas flow through the humidification vapor transfer unit (vapor transfer unit 2102 in FIG. 19A). Similarly, the humidity curve 2212 shows a relative humidity of about 70% at low flow rates, and the bypass unit 2120 in FIG. 19B, to which the curve corresponds, passes about 67% of its gas flow through the humidification vapor transfer unit.

Figure 21:
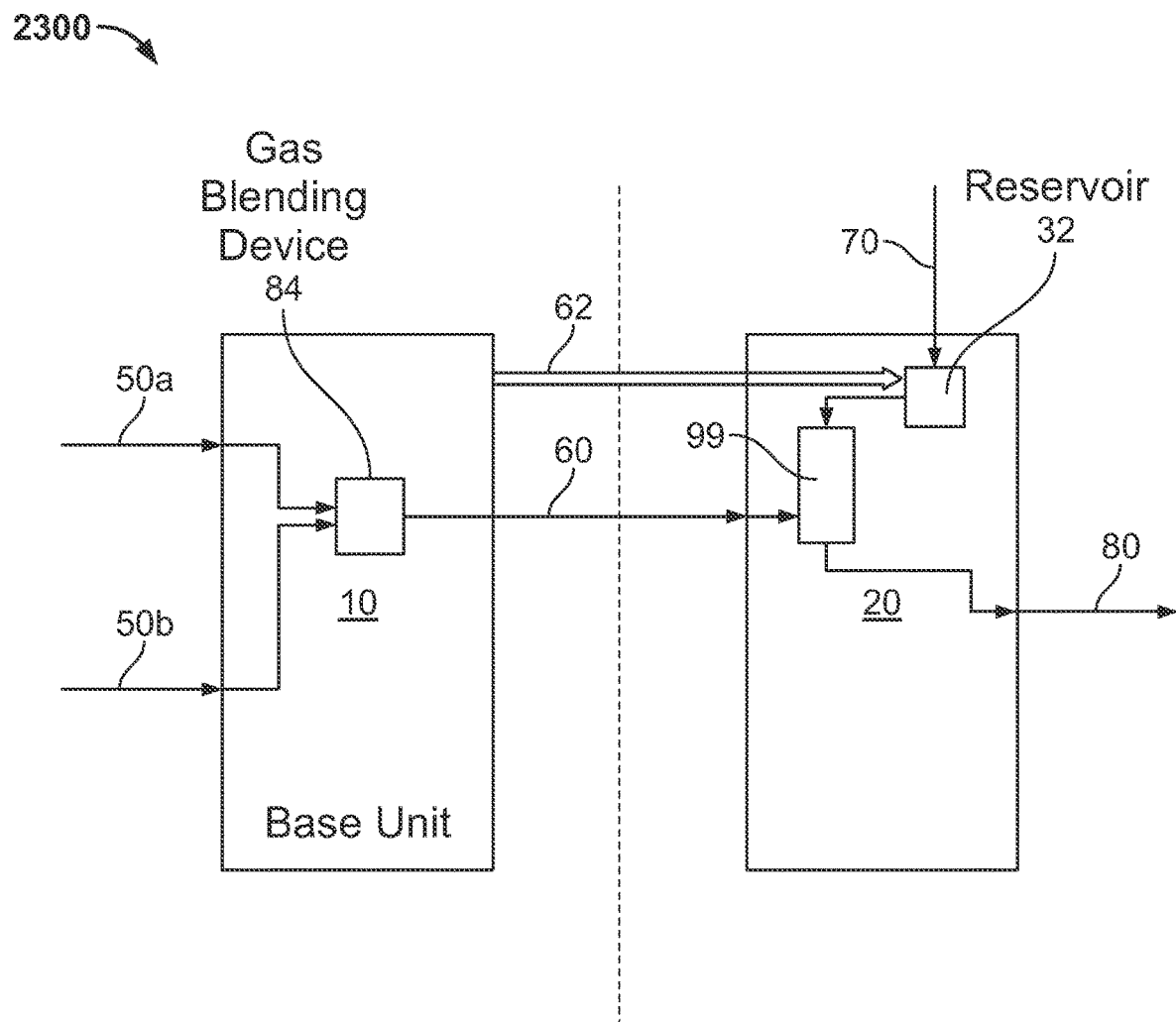
FIG. 21 shows a schematic representation of a humidification system, according to certain implementations.

The relative humidity curves 2206, 2208, 2210, 2212, and 2214 are all downward sloping because as flow rates increase, the gas passes more quickly through the humidification vapor transfer unit and has less time to receive humidity. However, the slopes of the humidity curves 2208, 2210, 2212, and 2214 are shallower than the slope of the humidity curve 2206. Thus, the bypass units 2100, 2120, 2140, and 2160 in FIGS. 19A-19D achieved more consistent humidification than the prior art system. The humidity curve 2208, which corresponds to the bypass unit 2160 in FIG. 19D having the orifice design, shows the shallowest slope and, therefore, the most consistent humidity level. The curve 2208 shows a relative humidity of about 85% relative humidity or lower at low flow rates (e.g., <15 L/min) and a relative humidity of between 75% and 80% at flow rates above 35 L/min. At the highest flow rates measured, about 40 L/min, the humidity curve 2208 shows a relative humidity within about 5% of the relative humidity of the humidity curve 2206 of the prior art system. Thus, the bypass unit 2160 having the orifice design exhibits a relative humidity at low flow rates low enough to prevent excessive humidification and condensation, while exhibiting humidity levels comparable to the prior art system at high flow rates. Thus, the bypass unit 2160 demonstrates that having a bypass passage with an orifice design can achieve acceptable performance at both high and low flow rates The systems, methods, and devices disclosed herein can be incorporated into a humidification system for a high flow therapy system such as humidification system 2300, which is schematically represented in FIG. 21. Humidification system 2300 delivers heated and humidified breathing gas 80 to a patient and includes a base unit 10 and a fluid pathway module 20. The illustrated base unit 10 includes controls for operating the humidification system 2300 and is configured to receive breathing gas 50a and 50b, such as medical air and oxygen, respectively. Alternatively, the controls may be remote from the base unit 10. In addition, other gases, such as, for example, helium, nitric oxide (INO), or any other suitable gas or combination of gasses, may be used. When different types of gas are received through the base unit 10, gases 50a and 50b may be blended by a gas blending device 84, to form blended gas 60, which is delivered to the fluid pathway module 20. While two different gases may be used with system 2300, those skilled in the art will recognize that the system 2300 may be used with only one gas, such as, for example air or pure oxygen, in which case the gas blending device 84 may be omitted.

The fluid pathway module 20 is releasably mounted to the base unit 10 and is configured to receive gas 60 from the base unit 10 and liquid 70 from an external water source. In an exemplary implementation, liquid 70 received by the fluid pathway module 20 is contained in a reservoir 32 to minimize potential contamination of the base unit 10 and to prime a pump used to circulate liquid 70. Liquid 70 contained in the reservoir 32 may be heated by a heat conduction 62 from the base unit 10. A vapor transfer unit 99 is releasably mounted to the fluid pathway module 20 and combines liquid 70 from reservoir 32 with blended gas 60 to supply heated and humidified breathing gas 80 to a patient. The vapor transfer unit 99 includes an apparatus for humidity control, and may be similar to the vapor transfer units 100, 300, 400, 700, or 1300 or bypass units 2100, 2120, 2140, or 2160 described above. In implementations in which the humidity level is controlled by making adjustments to the vapor transfer unit 99 (e.g., vapor transfer unit 700), access to the vapor transfer unit 99 is permitted without requiring removal of the vapor transfer unit 99 from the base unit 10. The vapor transfer unit 99 allows the humidity level of the humidified breathing gas 80 to be kept in an acceptable range throughout a wide range of gas flow rates (e.g., 5 L/min to 40 L/min). At low flow rates, the humidity level of the humidified breathing gas 80 is kept below levels that would cause condensation. Additionally, the humidity level of the humidified breathing gas 80 remains high enough at high flow rates to provide adequate levels of humidity for patient comfort. Thus, by incorporating the vapor transfer unit 99 for controlling humidity into the system 2300, the humidity of the humidified breathing gas 80 can be controlled.

Figure 22:
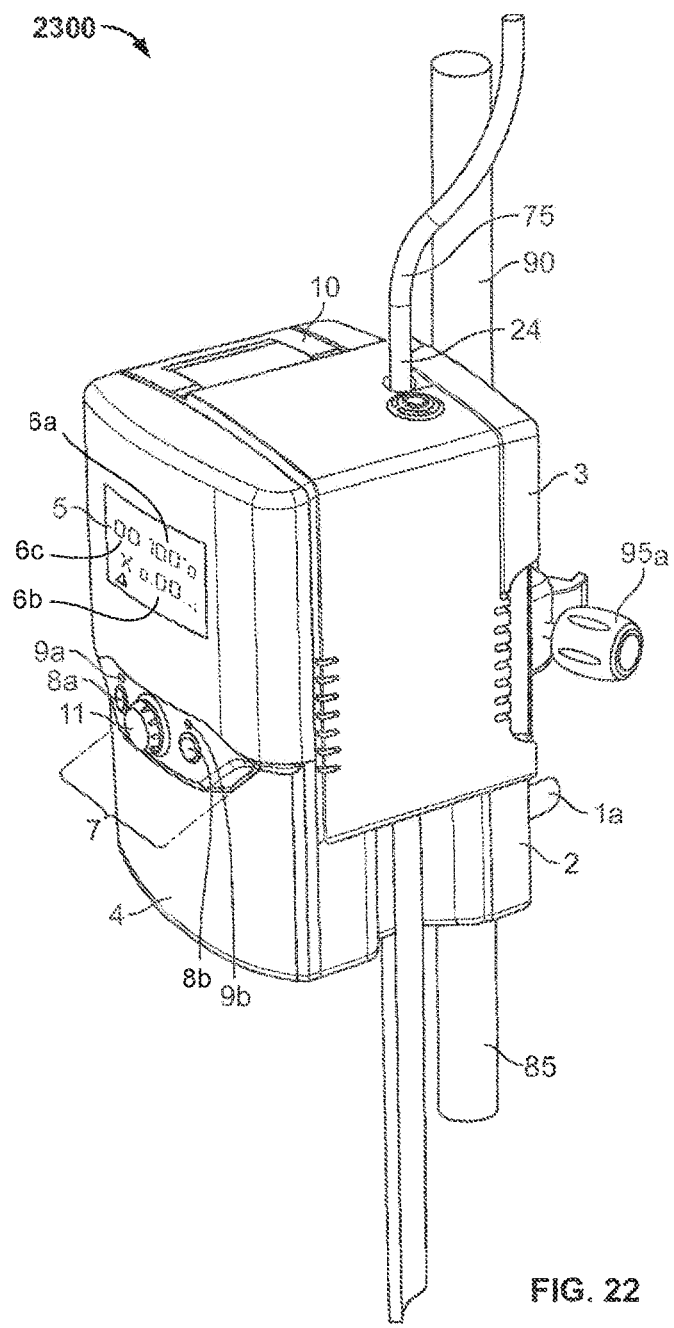
FIG. 22 shows a front perspective view of a humidification system, according to certain implementations.
Figure 23:
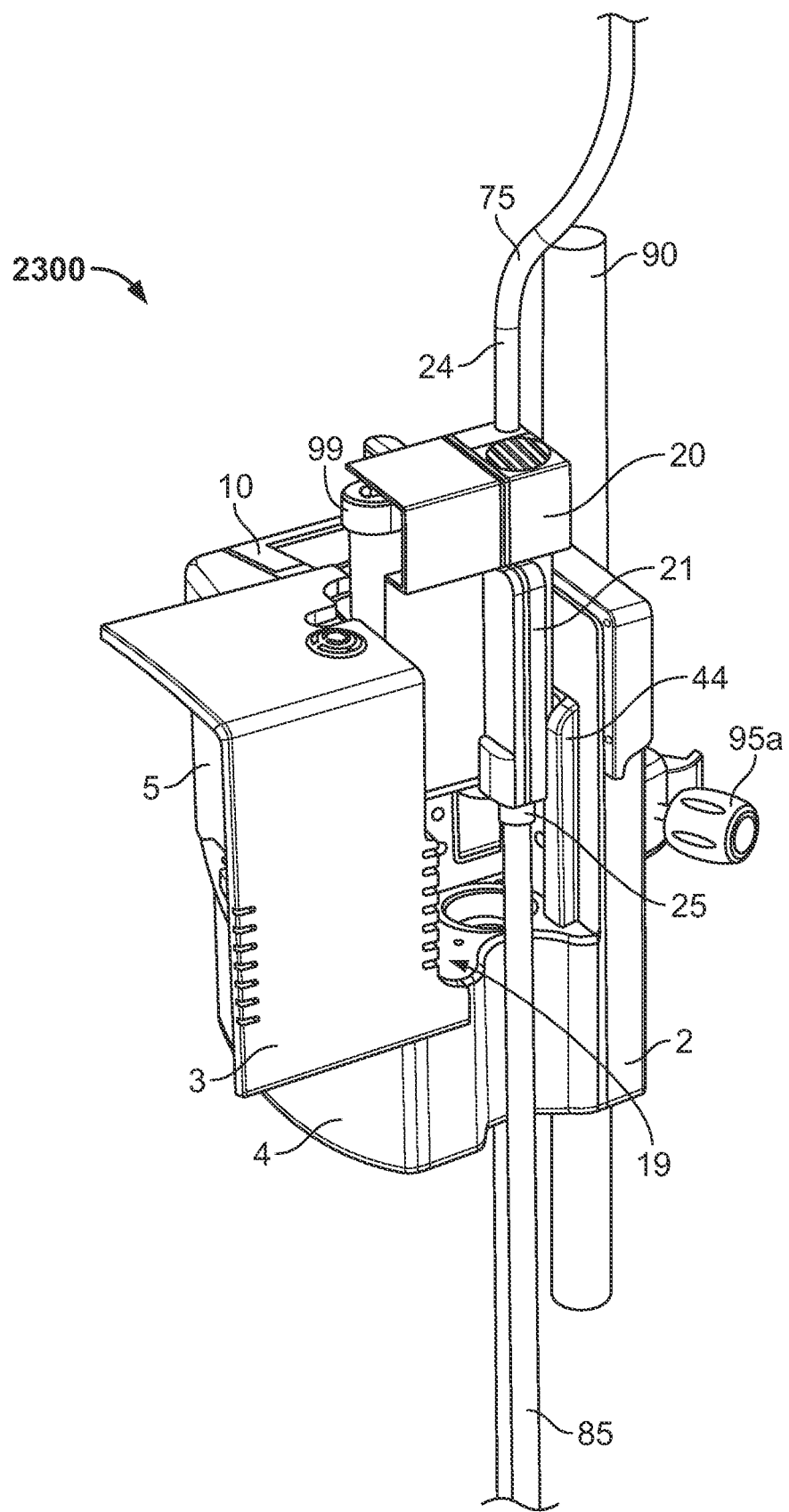
FIG. 23 shows a side perspective view of the humidification system of FIG. 22, according to certain implementations.

FIG. 22 shows a front perspective view of the humidification system 2300, and FIG. 23 shows a side perspective view of the humidification system 2300, according to certain implementations. The humidification system 2300 includes the base unit 10, which contains the controls that operate humidification system 2300 and is configured to operate without liquid flowing internally through the base unit 10 or being exchanged with the fluid pathway module 20. In some implementations, the base unit 10 is completely dry so that potential damage to electronics that control humidification system 2300 and bacterial contamination of the base unit 10 is minimized.

The base unit 10 is mountable to a stand 90, such as an IV pole, via mounting mechanism 95, shown in FIG. 3. In an exemplary implementation, a rear panel 2 of the base unit 10 includes a bracket 95b and a knob 95a that manipulates the bracket 95b to releasably secure the base unit 10 to the stand 90. When the knob 95a is rotated, for example, the bracket 95b may be tightened or loosened on the stand 90, thereby securing or loosening the humidification system 2300 with respect to the stand 90.

The rear of the base unit 10 further includes gas inlet ports with filters, such as port 1a, that are configured to connect to gas supply lines (not shown). The gas supply lines supply gas (such as medical air and oxygen) from a portable tank, compressor, or wall outlet into the base unit 10. In an exemplary implementation, gas supplied to the base unit 10 may be filtered and blended to provide a contaminant-free gas mixture. A gas blending device (not shown in FIGS. 22 and 23), for example, may be installed within the base unit 10 to blend gas being supplied into the base unit 10.

The side of the base unit 10 includes a door 3 that may be slid open or closed to expose or cover a component receiving portion 19 of the base unit 10. As shown in FIG. 22, the door 3 may be slid completely closed to cover the component receiving portion 19 from view. As illustrated in FIG. 23, door 3 is slid open to expose component receiving portion 19 of the base unit 10. When the door 3 is open, the fluid pathway module 20 can be releasably mounted or removed from the component receiving portion 19, e.g., using a handle 21. A guide 44 extends from the side of component receiving portion 19 to align and secure fluid pathway module 20 to base unit 10. FIG. 23 shows the fluid pathway module 20 partially installed on base unit 10.

When fluid pathway module 20 is mounted to the base unit 10, the fluid pathway module 20 is positioned to receive gas from the base unit 10. A gas outlet (not shown) of base unit 10 engages a gas inlet (not shown) of fluid pathway module 20 to form an airtight channel through which gas, received through the inlet port 1a, may be transferred to fluid pathway module 20. The fluid pathway module 20 is also configured to receive liquid from a liquid supply line 75 via liquid inlet 24. Liquid may be supplied to the fluid pathway module 20, for example, via a sterile water bag (not shown) that is suspended above the humidification system 2300. The sterile water bag may be punctured by a tube spike (not shown), with water being gravity fed from the water bag into the fluid pathway module 20 via a liquid supply line 75. An exemplary tube spike is disclosed in U.S. Pat. No. 7,654,507 owned by the Assignee of the present application, which is incorporated herein in its entirety by reference. Liquid is stored within the reservoir 32 (shown schematically in FIG. 21) in fluid pathway module 20 that is provided to receive liquid from the water bag as well as recirculated liquid. The liquid in fluid pathway module 20 does not flow through base unit 10. Liquid contained in the fluid pathway module 20 is vaporized in the vapor transfer unit 99 and combined with gas from the base unit 10 to generate the humidified breathing gas. As shown in FIG. 23, a delivery tube 85 is releasably coupled to a breathing gas outlet 25 of the fluid pathway module 20 to deliver humidified breathing gas to the patient.

As further illustrated in FIG. 22, the humidification system 2300 has a front panel 4 that includes a display panel 5, such as a liquid crystal display (LCD) or a light emitting diode (LED) display that provides visual indication of user settings and status conditions of the humidification system 2300. The user settings may include user adjustable settings such as temperature 6a, flow rate 6b, and oxygen saturation level 6c of the breathing gas to be delivered to the patient. User settings may be adjusted, for example, via a user interface 7. The user interface 7 includes buttons 8a, 8b, LEDs 9a, 9b, and a knob 11 to adjust and monitor operating conditions of humidification system 2300. In some implementations, the user interface may be used to configure the vapor transfer unit 99 for a flow rate without removing the vapor transfer unit 99 from the base unit. For example, if the vapor transfer unit 99 includes a valve for obstructing a subset of tubes within the vapor transfer unit 99, the user interface may allow the user to control the valve and thus change the subset of tubes obstructed by the vapor transfer unit 99. By configuring the vapor transfer unit 99 for operation at high and low flow rates while the vapor transfer unit 99 remains inside the humidification system 2300, a single vapor transfer unit can be used for operation over a wide range of flow rates. The use of a single vapor transfer unit can prevent the interruption of therapy associated with switching vapor transfer units in prior art systems when flow rates are alternated between high and low flow rates.

Figure 24:
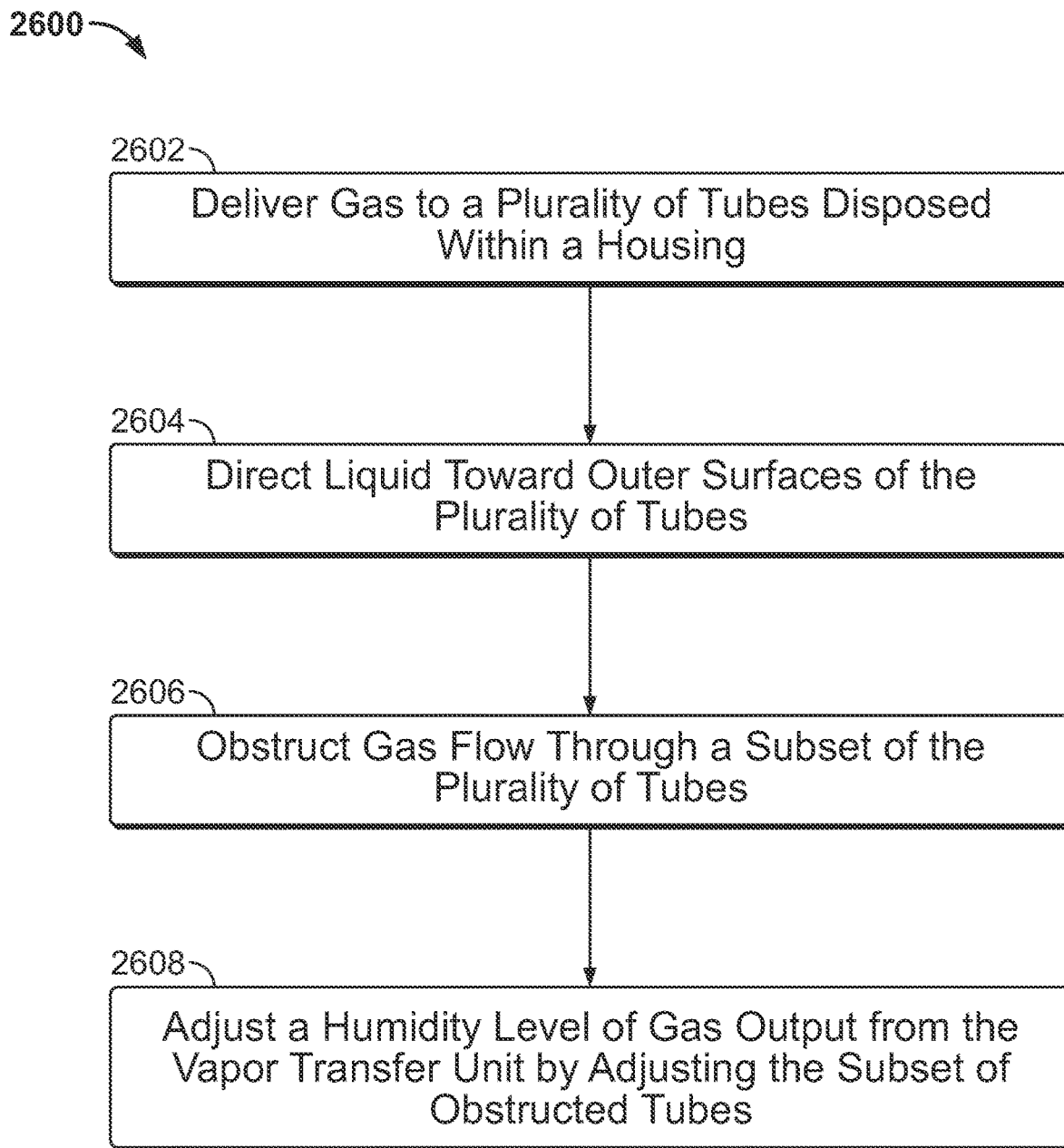
FIG. 24 shows an illustrative process for controlling the humidity of a breathing gas by obstructing a subset of tubes, according to certain implementations.

FIG. 24 shows an illustrative process 2600 for controlling the humidity of a breathing gas by obstructing a subset of tubes, according to certain implementations. The process 2600 may be performed using the vapor transfer unit 400, the vapor transfer unit 700, the vapor transfer unit 1300, or any other suitable vapor transfer unit. In step 2602, gas is delivered to a plurality of tubes disposed within a housing. The gas may be delivered at a high flow rate (e.g., >5 L/min, >8 L/min, >10 L/min, >15 L/min, >20 L/min, >30 L/min, 40 L/min, or any other suitable flow rate). In some implementations, a first group of the tubes are porous and a second group of the tubes are non-porous. Liquid is directed toward outer surface of the plurality of tubes in step 2604. In step 2606, the gas flow through a subset of the plurality of tubes is obstructed. The humidity level of gas output from the vapor transfer unit is adjusted by adjusting the subset of obstructed tubes in step 2608. In some implementations, adjusting the subset of obstructed tubes is performed by changing a ratio of the number of unobstructed porous tubes to the number of unobstructed non-porous tubes from a first ratio to a second ratio. In certain implementations, the first ratio is greater than 50 and the second ratio is less than 25. In some implementations, adjusting the subset of obstructed tubes is performed by changing a total number of obstructed tubes. By adjusting the subset of obstructed tubes, the humidity level of gas output may be controlled.

Figure 25:
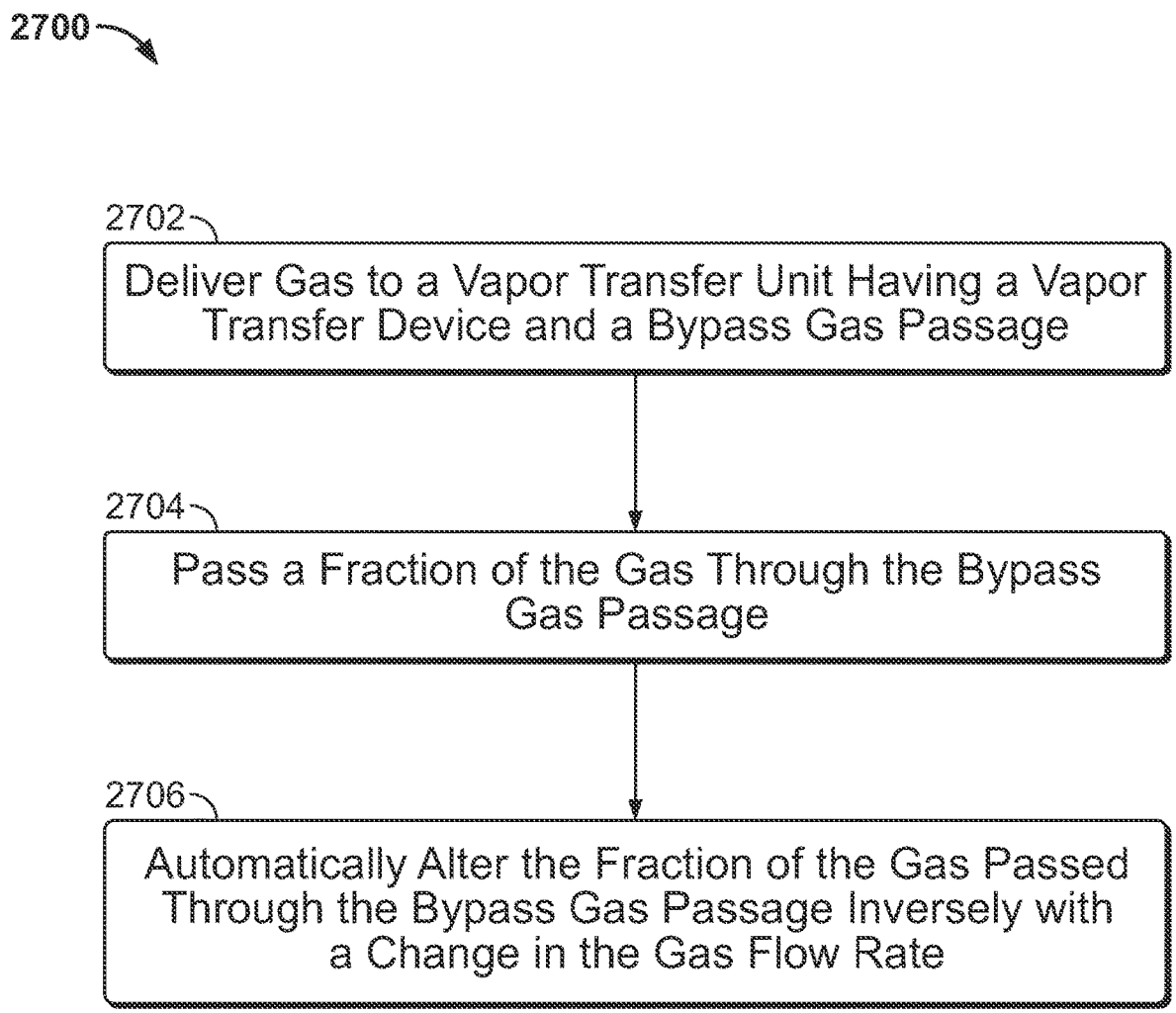
FIG. 25 shows an illustrative process for automatically controlling the humidity of a breathing gas, according to certain implementations.

FIG. 25 shows an illustrative process 2700 for automatically controlling the humidity of a breathing gas, according to certain implementations. The process 2700 may be performed by the vapor transfer unit 100, bypass unit 2160, or any other suitable vapor transfer unit. In step 2702, gas is delivered to a vapor transfer unit having a vapor transfer device and a bypass gas passage. Liquid may also be delivered to the vapor transfer device to humidify the breathing gas. In certain implementations, the vapor transfer device includes a plurality of hollow fiber membranes for humidifying the breathing gas. A fraction of the incoming gas is passed through the bypass gas passage in step 2704. The fraction of gas passed through the bypass gas passage bypasses the vapor transfer device. In step 2706, the fraction of the gas passed through the bypass gas passage is automatically altered inversely with a change in the gas flow rate. Thus, when the gas flow rate increases, the fraction of bypassed gas decreases. Conversely, when the gas flow rate decreases, the fraction of bypassed gas increases. The internal dimensions of the vapor transfer unit remain fixed as the flow rate changes. Thus, the change in the fraction of bypassed gas is not achieved by manipulating a valve, but is a function of the fixed dimensions of the bypass passage.

In some implementations, passing the fraction of the gas through the bypass gas passage includes passing gas through a constriction sized so that the fraction of gas received by the bypass gas passage decreases as the gas flow rate increases. In certain implementations, the constriction has a diameter of 0.040 in (1 mm). By automatically altering the fraction of gas that is bypassed, the humidity level of an output gas can be kept within an acceptable range without the need for human intervention.

Figure 26:
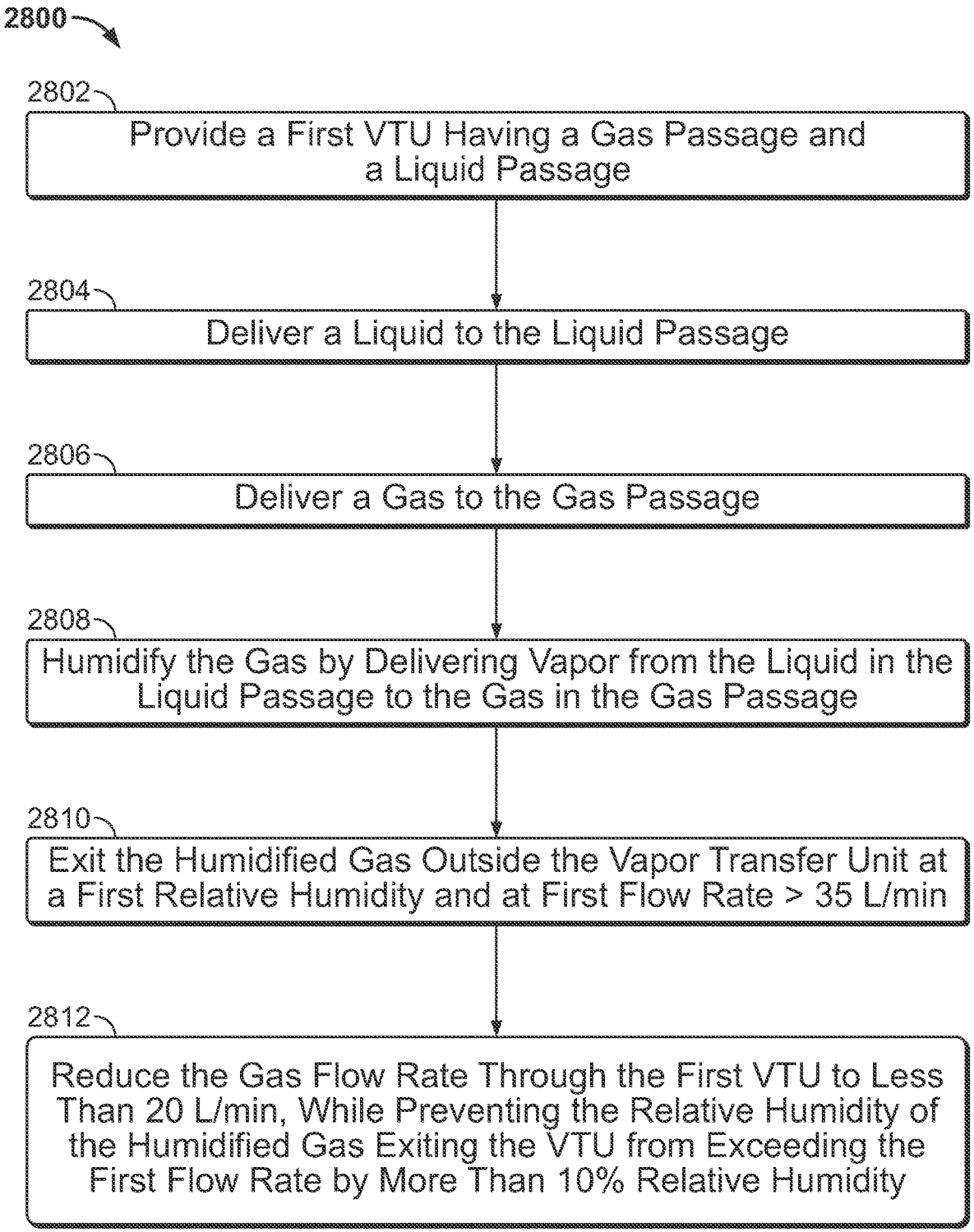
FIG. 26 shows an illustrative process for controlling the humidity of a breathing gas, according to certain implementations.

FIG. 26 shows an illustrative process 2800 for controlling the humidity of a breathing gas, according to certain implementations. The process 2800 may be performed using the vapor transfer units 100, 300, 400, 700, or 1300 or bypass units 2100, 2120, 2140, or 2160. In step 2802, a first vapor transfer unit having a gas passage and a liquid passage is provided. A liquid is delivered to the liquid passage in step 2804. In step 2806, a gas is delivered to the gas passage. The gas is humidified by delivering vapor from the liquid in the liquid passage to the gas in the gas passage in step 2808. In step 2810, the humidified gas is exited from the vapor transfer unit at a gas flow rate greater than 35 liters per minute at a first relative humidity. In some implementations, the gas is humidified to a high relative humidity (e.g., 70%, >70%, >75%, >80%, >85%, >90%, or any other suitable relative humidity). In step 2812, the gas flow rate through the first vapor transfer unit is reduced to less than 20 liters per minute, while the relative humidity of the output gas is prevented from exceeding the first relative humidity by more than a margin, such as 10% relative humidity. The margin may be any other suitable small value (e.g. 20%, 15%, 12%, 8%, 7%, 6%, or 5% relative humidity). Preventing the relative humidity of the output gas from exceeding 99.5% may prevent condensation. By reducing the flow rate while preventing a large change in the relative humidity of the output, a single vapor transfer unit can be used for therapy at high and low flow rates to deliver gas at a consistent relative humidity below saturation. The use of a single vapor transfer unit can thus eliminate or reduce the interruption in therapy caused by changing vapor transfer units.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in high flow therapy systems, may be applied to systems, devices, and methods to be used in other ventilation circuits.

Variations and modifications will occur to those of skill in the art after reviewing this disclosure. For example, it can be beneficial to heat the gas that bypasses humidification. Since the humidified gas is heated, mixture with unheated bypass gas could cause a reduction in the temperature of the output gas depending on the fraction of the gas that is bypassed. Heating the bypass gas could result in an output gas temperature that does not depend on the fraction of flow that is bypassed. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

We claim:

1. A system for humidifying a breathing gas, the system comprising:
   a housing having a liquid inlet, a liquid outlet, a gas inlet, and a gas outlet;
   a vapor transfer compartment disposed within the housing and having:
      a first gas passage coupling the gas inlet to the gas outlet;
      a liquid passage coupling the liquid inlet to the liquid outlet; and
      a permeable membrane separating the first gas passage and the liquid passage; and
   a bypass gas passage disposed externally to the housing and coupling the gas inlet to the gas outlet, the bypass gas passage being configured to receive a fraction of the gas received by the gas inlet, wherein the bypass gas passage is configured to automatically alter the fraction of gas passed through the bypass gas passage, and wherein the fraction of gas passed through the bypass gas passage is solely a function of fixed dimensions of the bypass gas passage.

2. The system of claim 1, wherein the bypass gas passage comprises a constriction configured to provide resistance to gas flow.

3. The system of claim 2, wherein a cross-sectional area of the constriction is fixed.

4. The system of claim 3, wherein the permeable membrane comprises a plurality of hollow fiber membranes.

5. The system of claim 4, wherein the first gas passage is defined by internal walls of the plurality of hollow fiber membranes.

6. The system of claim 5, wherein the liquid inlet is formed in the housing and is positioned to direct liquid toward outer surfaces of the hollow fiber membranes and the liquid outlet is positioned to direct liquid from the housing.

7. The system of claim 2, wherein the constriction comprises a protrusion that narrows a portion of the bypass gas passage.

8. The system of claim 2, wherein the constriction automatically alters the fraction of gas passed through the bypass gas passage inversely with a change in a flow rate of the breathing gas.

9. The system of claim 2, wherein the construction is ring-shaped.

10. The system of claim 2, wherein the constriction is sized so that the fraction of gas received by the bypass passage decreases as a rate of gas flow into the gas inlet increases.

11. The system of claim 1, wherein the bypass gas passage is a tube.

12. The system of claim 1, wherein the bypass gas passage is disposed parallel to the first gas passage.

13. The system of claim 1, wherein the bypass gas passage is configured to automatically alter the fraction of gas passed through the bypass gas passage inversely with a change in the flow rate of the breathing gas.

14. A method for humidifying a breathing gas, the method comprising:

providing a housing having a liquid inlet, a liquid outlet, a gas inlet, and a gas outlet;

providing a vapor transfer compartment disposed within the housing, the vapor transfer compartment having:

a first gas passage coupling the gas inlet to the gas outlet;

a liquid passage coupling the liquid inlet to the liquid outlet; and a permeable membrane separating the first gas passage and the liquid passage;

delivering the breathing gas to the gas inlet at a gas flow rate;

passing a fraction of the breathing gas delivered to the gas inlet through a bypass gas passage, wherein the bypass gas passage is disposed externally to the housing and couples the gas inlet to the gas outlet, wherein the bypass gas passage is configured to automatically alter the fraction of gas passed through the bypass gas passage, and wherein the fraction of gas passed through the bypass gas passage is solely a function of fixed dimensions of the bypass gas passage; and humidifying the breathing gas within the vapor transfer compartment.

15. The method of claim 14, comprising directing the breathing gas to an upstream end of the first gas passage via the gas inlet.

16. The method of claim 14, comprising directing a breathing gas output from a downstream end of first gas passage via the gas outlet.

17. The method of claim 14, comprising delivering the breathing gas to the gas inlet with the gas flow rate being greater than 8 liters per minute.

18. The method of claim 14, comprising outputting the breathing gas from the gas outlet with the flow rate of the breathing gas being greater than 35 liters per minute at a first relative humidity.

19. The method of claim 14, wherein passing the fraction of the breathing gas through the bypass gas passage comprises passing the breathing gas through a constriction configured to provide resistance to gas flow.

20. The method of claim 19, wherein the constriction comprises a protrusion that narrows a portion of the bypass gas passage.

21. The method of claim 19, wherein the constriction automatically alters the fraction of the breathing gas passed through the bypass gas passage inversely with a change in the flow rate of the breathing gas.

22. The method of claim 14, wherein the bypass gas passage is configured to automatically alter the fraction of gas passed through the bypass gas passage inversely with a change in the flow rate of the breathing gas.

* * * * *